US012714783B2

(12) United States Patent
Bussiere et al.

(10) Patent No.: US 12,714,783 B2
(45) Date of Patent: Aug. 25, 2026

(54) DRUG DELIVERY SYSTEM

(71) Applicant: INSULET CORPORATION, Acton, MA (US)

(72) Inventors: John Richard Bussiere, Littleton, MA (US); Eduardo Luis Latouche, Chelsea, MA (US); Seyedmohammadali Aghvami, Newton, MA (US); Renwei Liu, Woburn, MA (US)

(73) Assignee: INSULET CORPORATION, Acton, MA (US)

( * ) Notice: Subject to any disclaimer, the term of this patent is extended or adjusted under 35 U.S.C. 154(b) by 628 days.

(21) Appl. No.: 18/032,636

(22) PCT Filed: Oct. 1, 2021

(86) PCT No.: PCT/US2021/053225
§ 371 (c)(1),
(2) Date: Apr. 19, 2023

(87) PCT Pub. No.: WO2022/086697
PCT Pub. Date: Apr. 28, 2022

(65) Prior Publication Data

US 2023/0381405 A1 Nov. 30, 2023

Related U.S. Application Data

(60) Provisional application No. 63/094,602, filed on Oct. 21, 2020.

(51) Int. Cl.
*A61M 5/142* (2006.01)
*A61M 5/162* (2006.01)

(52) U.S. Cl.
CPC ........ *A61M 5/14244* (2013.01); *A61M 5/162* (2013.01)

(58) Field of Classification Search
CPC .................. A61M 5/155; A61M 5/145; A61M 2005/247; A61J 1/20; A61J 1/2003; A61J 1/2006; A61J 1/2096
See application file for complete search history.

(56) References Cited

U.S. PATENT DOCUMENTS 5,398,850 A * 3/1995 Sancoff ...................... B01J 7/02 222/399
9,833,579 B2 12/2017 Pedersen et al.
(Continued)

FOREIGN PATENT DOCUMENTS

EP 2223714 A1 9/2010
KR 20120105718 A 9/2012
(Continued)

OTHER PUBLICATIONS

International Search Report and Written Opinion for International Application No. PCT/US2021/053225 dated Jan. 28, 2022.
(Continued)

*Primary Examiner* — Nilay J Shah
(74) *Attorney, Agent, or Firm* — Goodwin Procter LLP

(57) ABSTRACT

Methods and devices for dispensing a therapeutic composition from within a sealed container and drug delivery systems are described. The device and the method for dispensing a therapeutic composition from within a sealed container comprises a container configured to hold a therapeutic composition and include a first septum, a needle, a tube and an expandable membrane configured to expand out of the tube into an interior volume of the container to displace the therapeutic composition out of the container through the needle.

20 Claims, 22 Drawing Sheets

(56) References Cited

U.S. PATENT DOCUMENTS

| | | | | |
|---|---|---|---|---|
| 2005/0209562 | A1 | 9/2005 | Kim | |
| 2012/0123382 | A1 | 5/2012 | Kubo | |
| 2014/0276587 | A1 | 9/2014 | Imran | |
| 2015/0335829 | A1* | 11/2015 | Giambattista ....... | A61M 5/3146 604/192 |
| 2016/0287812 | A1 | 10/2016 | Nielsen et al. | |
| 2017/0196773 | A1 | 7/2017 | Fangrow et al. | |
| 2018/0110922 | A1* | 4/2018 | Dunki-Jacobs ....... | A61J 1/2075 |
| 2018/0272073 | A1 | 9/2018 | Giambattista et al. | |
| 2018/0361078 | A1 | 12/2018 | Young | |
| 2019/0009939 | A1 | 1/2019 | Py | |
| 2019/0091404 | A1 | 3/2019 | Nazzaro et al. | |
| 2019/0328968 | A1 | 10/2019 | Giambattista | |
| 2022/0280385 | A1* | 9/2022 | Converse .......... | A61M 5/14248 |

FOREIGN PATENT DOCUMENTS

| | | | |
|---|---|---|---|
| WO | WO 2020/169842 | A1 | 8/2020 |
| WO | WO 2021/016567 | A1 | 1/2021 |

OTHER PUBLICATIONS

International Preliminary Report on Patentability (Chapter 1) for International Application No. PCT/US2021/053225 dated May 4, 2023.

* cited by examiner

DRUG DELIVERY SYSTEM

CROSS-REFERENCE TO RELATED APPLICATIONS

This application is a national stage filing under 35 U.S.C. § 371 of International Patent Application Serial No. PCT/US2021/053225, filed Oct. 1, 2021, which claims priority to U.S. Provisional Application Ser. No. 63/094,602, filed Oct. 21, 2020. The entire contents of these applications are incorporated herein by reference in their entirety.

FIELD

Disclosed embodiments are related to drug delivery systems.

BACKGROUND

Drug delivery systems are oftentimes used for delivering a desired composition, such as a therapeutic compound, to a subject over long-duration periods. Depending on the particular application, drug delivery systems may either be used to deliver the desired composition subcutaneously, epidurally, and/or intravenously. Drug delivery systems are typically used for delivering these compositions to subjects where either continuous and/or repeated infusions of the composition are desired for a particular treatment. For example, certain conditions such as diabetes, cancer, chronic pain, infections, gastrointestinal conditions and others may benefit from treatments using drug delivery systems.

SUMMARY

In some embodiments, a device includes a container configured to hold a therapeutic composition, the container including a first septum, a needle, a tube, and an expandable membrane disposed at least partially in the tube. The container is configured to be displaced towards the needle and the tube to pierce the first septum of the container with the needle and the tube. When the tube pierces the first septum, the expandable membrane is configured to expand out of the tube into an interior volume of the container to displace the therapeutic composition out of the container through the needle.

In some embodiments, a method for expelling a therapeutic composition from a container includes piercing a first septum of the container with a needle and a tube, expanding a flexible membrane from the tube into an interior volume of the container to pressurize an interior volume of the container, and flowing the therapeutic composition out of the interior volume of the container through the needle.

In some embodiments, a device includes a housing and a container disposed in the housing and configured to hold a therapeutic composition. The container includes a first septum disposed on a first surface of the container. The device also includes a drive system operatively connected to container. The drive system includes a drive housing including a first drive housing portion and a second drive housing portion. The drive system also includes a lock including a first lock portion associated with the first drive housing portion and a second lock portion associated with the second drive housing portion. The lock selectively retains the first drive housing portion and the second drive housing portion in a first retracted configuration when the lock is in a locked configuration. The drive system also includes a mechanical potential energy source disposed in the drive housing between the first drive housing portion and the second drive housing portion. When the lock is moved to an unlocked configuration, the mechanical potential energy source displaces the second drive housing portion to displace the container.

In some embodiments, a method of expelling a therapeutic composition from a container includes restraining a first portion of a drive housing to avoid applying a driving force to the container, unlocking the drive housing to release the first drive housing portion, and displacing the first drive housing portion against the container to displace the container.

In some embodiments, a drug delivery system includes a drug delivery device including at least one reservoir configured to hold a therapeutic composition and a first septum associated with the at least one reservoir, and a filling device configured to couple with the drug delivery device. The filling device includes a filling device housing, a container disposed in the filling device housing and configured to hold the therapeutic composition, the container comprising a second septum. The drug delivery system also includes at least one filling needle having a first end configured to pierce the first septum and a second end configured to pierce the second septum. The at least one filling needle is initially attached to the drug delivery device or the filling device. The drug delivery system also includes a first alignment structure associated with the drug delivery device and a second alignment structure associated with the filling device housing. The first alignment structure and the second alignment structure are configured to engage to align the first end of the at least one filling needle with the first septum or the second end of the at least one filling needle with the second septum. When the first alignment structure and the second alignment structure are engaged, the at least one filling needle is in fluid communication with the at least one reservoir. The filling device is configured to displace the container towards the second end of the at least one filling needle to pierce the second septum and place the container in fluid communication with the at least one reservoir.

In some embodiments, a method for filling a drug delivery device with a therapeutic composition includes attaching a filling device to a drug delivery device including at least one reservoir configured to receive the therapeutic composition. When the filling device is attached to the drug delivery device, at least one filling needle is in fluid communication with the at least one reservoir. The method also includes displacing a container contained in the filling device towards the at least one filling needle to pierce a septum of the container with the at least one filling needle and to place the container in fluid communication with the at least one reservoir through the at least one filling needle.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
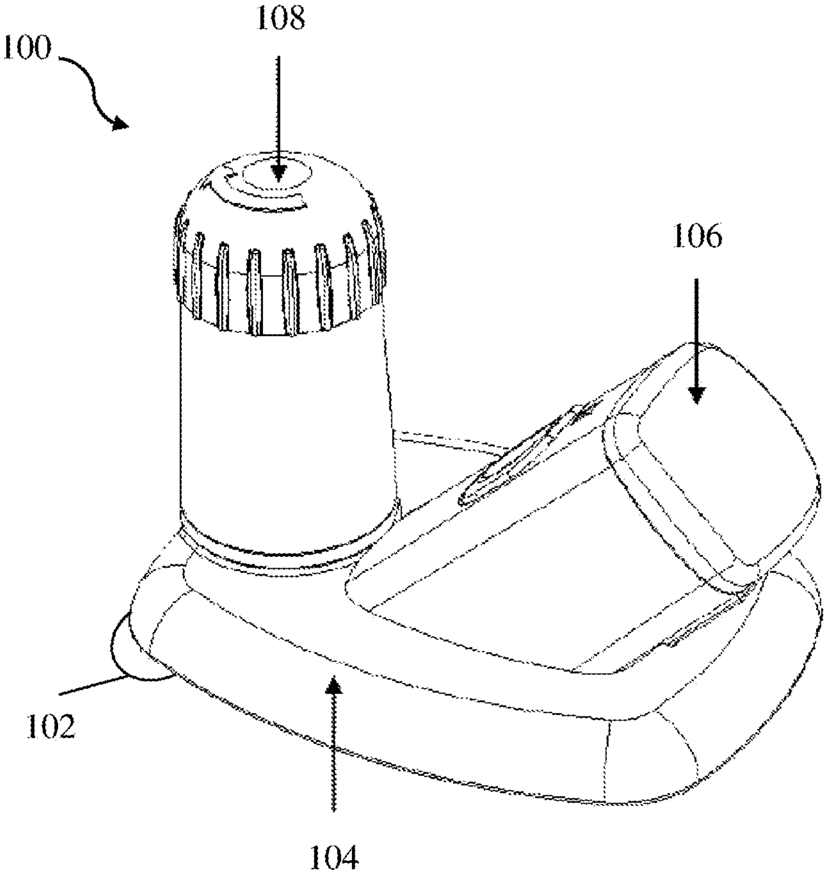
FIG. 1 is a schematic perspective view of a drug delivery system according to one embodiment.

Drug delivery systems, including wearable or on-body drug device systems ("OBDDS"), have become an increasingly popular method of drug delivery. The systems may include devices that are worn on a person's body for anywhere from a single day to multiple days at a time. Thus, it may be desirable for the devices to be as small and unobtrusive as possible for the user. The size of the device depends on the volume of the therapeutic agent to be contained and delivered to the patient during its indicated use. Most wearable devices contain up to 2 mL of liquid volume held in custom designed rigid containers, where 2 ml is the threshold volume for an acceptably low profile of the device, though instances in which smaller and/or larger volumes are used in a device are also contemplated. Pharmaceutical businesses have developed and evolved highly efficient production lines for "fill to finish" (dispensing, containment, sterilization, storage and transport) processing of liquid therapeutic agents in industry standardized cylindrical geometries of cartridges and vials. However, these standardized containers are generally too large to be integrated with low profile and small footprints of typical body-worn pumps. Accordingly, the inventors have recognized the benefits of devices that are capable of delivering therapeutic compositions from pre-filled containers, cartridges and vials to a desired target location including, for example, the reservoir of a drug delivery device to simplify the filling process of such a device by an end user. Additionally, the inventors recognized that the ability to maintain the pre-filled containers in an aseptic sealed state prior to use while permitting simple quick actuation by a user may also be desirable. Accordingly, the various embodiments described herein may exhibit both these as well as other potential benefits. However, embodiments in which benefits different from those noted herein are also possible as the disclosure is not limited to only providing these benefits.

In view of the above, in some embodiments, a drug delivery system may include a drug delivery device to administer a therapeutic agent to a patient and a changeable filling device to dispense the therapeutic agent into a reservoir of the drug delivery device. The filling device may be sized to accept industry standardized containers, such as a standard pre-filled cartridge or vial, containing a desired volume of therapeutic component. Such a filling device may help to seamlessly integrate pharmaceutical drug manufacturing and delivery processes with wearable drug devices. The pre-prepared filling device may be attached to the drug delivery device and later removed after it dispenses the therapeutic composition volume into the reservoir. Thus, in some embodiments, a filling device may be used to provide a therapeutic composition to a drug delivery device using standard containers, such as standard vials. However, the final wearable device may have any desired profile for a given application including, for example, a low profile and/or small footprint in some embodiments.

In some embodiments, a drug delivery system may include a filling needle configured to fluidly connect a filling device and a reservoir in a drug delivery device. The filling needle may have a first end to pierce a septum on the drug delivery device and a second end to pierce a septum on the cartridge or vial, or other container including a therapeutic composition, included in the filling device. The drug delivery system may also include alignment structures on the drug delivery device and the filling device that are configured to engage with one another to align the first end of the at least one filling needle with the drug delivery device septum and/or the second end of the filling needle with the septum of the container including the therapeutic composition. When the filling needle has pierced each septum, the cartridge or vial and the reservoir are placed in fluid communication with each other through the filling needle and the therapeutic component may flow from the cartridge or vial into the reservoir when the contents of the cartridge or vial are pressurized using any of the methods and/or construction including those detailed herein.

The inventors have further recognized that in some embodiments a drug delivery device may be used with either larger volumes and/or higher viscosity therapeutic compositions. Accordingly, in such embodiments, a drive system used to dispense the therapeutic composition from the filling device may apply an initial force that is larger than typically used for dispensing a therapeutic composition during deployment. The use of these larger initial forces may cause a device to be more susceptible to creep, and thus, applying an undesired force and/or displacement to a container including a therapeutic composition prior to actuation.

In view of the above, the inventors have recognized the benefits associated with a drive system that is configured to avoid applying forces directly to a container including a therapeutic composition and/or that minimizes creep while the device is in the unactuated configuration. In one such embodiment, the drive system of a filling device may include a housing that contains a mechanical potential energy source (or other energy source), such as a compressed spring or elastic component. The drive system may include a release key that, upon activation, converts the potential energy into kinetic energy by releasing the spring. The potential energy source then displaces the released portion of the drive system to apply a force on the vial causing it to be axially displaced toward a filling needle to pierce the cartridge or vial's septum. Once the septum is pierced, the therapeutic agent may flow through the filling needle as described elsewhere herein.

In some embodiments, to help avoid undesirable creep and application of a force to and/or a displacement of a container including a therapeutic composition, a device may include a container configured to hold the therapeutic composition, and the container may include a first septum. A drive system disposed within an interior of a housing of the device may be arranged proximate to a portion of the container removed from the septum including, for example, on a side of the container opposite from the first septum of the container. The drive system may include a drive housing the first drive housing portion and a second drive housing portion that are selectively locked to one another by an associated block. A mechanical potential energy source, such as a spring or compressed elastic component may be disposed between the first and second portions of the drive housing such that the first and second portions of the drive housing are biased away from one another. The lock may prevent the first and second portions of the drive housing from being moved relative to one another in the locked configuration and may permit the relative movement of the first and second portions of the drive housing when in the unlocked configuration. In some embodiments, the drive housing may be retained in a first retracted configuration in which the first and second portions of the drive housing are proximate to, or in contact with, one another and a second extended configuration which the first and second portions of the drive housing are distance from one another. Accordingly, the lock may restrain a portion of the drive housing from being be displaced towards an associated container including a therapeutic composition when in a locked configuration and may permit the portion of the drive system to be released to apply a force to the container to displace in a desired direction, including, for example, towards a needle to pierce the septum of the container with the needle. For instance, the released portion of the drive housing may be displaced against a portion of the container to provide the desired displacement.

It should be understood that any appropriate source of mechanical potential energy such as a spring, compressed elastic component, or any other appropriate component capable of storing mechanical potential energy that may be released to displace to components away from one another. Specific examples of appropriate mechanical potential energy sources may include, but are not limited to, a helical compression spring, a conical spring, a torsion spring, a compressed elastic material, and/or any other appropriate construction as the disclosure is not so limited.

While some therapeutic compositions are provided in containers including a displaceable piston, other therapeutic compositions are manufactured and distributed in containers only including a septum. Accordingly, the inventors have recognized the benefits associated with devices capable of integrating such a container into an easy to use device for dispensing the therapeutic composition without modifying the container. For instance, in some embodiments, an expandable membrane may be deployed into an interior of a container including a therapeutic composition to pressurize the interior volume of the container. This may be combined with a needle in fluid communication with the interior volume to dispense the therapeutic composition out of the container to a desired location. Depending on the specific application, such a dispensing method may be used with a filling device for dispensing the therapeutic composition into an associated drug delivery device and/or directly into the tissue of a subject as the disclosure is not limited in this fashion.

In one embodiment a device including an expandable membrane may include a dispensing needle and a tube with an expandable membrane at least partially disposed in the tube. The tube may be any hallow tubular structure with blunt and/or sharp ends, and may have any appropriate cross-sectional shape and/or may follow any appropriate path along its length depending on the desired application. The dispensing needle and the tube may both have a piercing end facing the septum of an associated container including a therapeutic composition. In some embodiments, the expandable membrane may be connected to a reaction chamber that contains chemically reactive substances that when mixed, generate a gas reaction within the chamber and expands the expandable membrane out of the tube and into an interior volume of the container when the septum of the container has been pierced by the dispensing needle and tube. By expanding the expandable membrane into an interior of the container, the interior volume may be pressurized causing the therapeutic composition to be displaced out of the vial through the first filling needle.

In order to actuate generation of the gas at a desired point to deploy an expandable membrane, may be desirable to include an appropriate trigger in the device. While any appropriate trigger and corresponding reaction chamber may be used, in some embodiments, it may be desirable to use a frangible barrier that separates the reaction chamber into a first volume including a first reactant and a second volume including a second reactant. Thus, when the frangible barrier is broken, the first and second reactants may mix within the combined volume of the reaction chamber to produce the desired gas. While various constructions may be used, in some embodiments, the tube including the expandable membrane disposed therein may be operatively coupled to the frangible barrier. Accordingly, when a force, such as the piercing force applied as the tube pierces through a septum of an associated container, may apply a force to the tube and frangible barrier causing the barrier to break and thus functioning as a trigger for the desired gas generation. Of course, different types of methods for generating gas as well as a triggering the gas generation may be used as the disclosure is not so limited. For example, compressed gas, such as a compressed $CO_2$ cylinder, may also be used. The device may include a drive system as described above that, when activated, displaces the container toward the dispensing needle and tube so that the dispensing needle and tube pierce the septum and the tube fractures the frangible barrier to allow the two reactants to mix and generate a gas reaction.

In some embodiments, the chemically reactive substances stored in the isolated sealed volumes of the reaction chamber may include acid and base combinations such as potassium carbonate ($K_2CO_3$) and citric acid ($C_6H_8O_7$) with ratio (by volume) in the range of 1 to 4 or 1 to 6, but not restricted to such. Other appropriate types of acid and base combinations may include, but are not limited to, acetic acid and sodium carbonate and potassium carbonate. Other types of reactions to generate gas may also be used including, for example, an appropriate amount of explosive material that may be ignited to generate a desired amount of gas. However, regardless of the specific reaction, the amount of generated gas may be sufficient to expand the associated expandable membrane to a desired volume and pressure to dispense the associated therapeutic composition. Additionally, in some embodiments compressed gas from a compressed gas source, such as a compressed gas cylinder associated with a valve, trigger, or other system that is capable of selectively delivering gas to deploy the membrane. Accordingly, it should be understood that the current disclosure is not limited to the specific method for generating, providing, and/or triggering of the gas.

It should be understood that the expandable membranes used in the various embodiments described herein may correspond to any appropriate flexible membrane capable of being deformed from within the interior of a tube into the interior of a container to pressurize the interior of the container. Appropriate types of membranes may include, but are not limited to, membranes with thicknesses that are between or equal to 0.0127 mm and 0.203 mm. Appropriate types of material may also include flexible materials such as polyisoprene, silicone, latex, polyurethane, or similar. An expandable membrane may also have any appropriate shape prior to being deformed in order to initially fit within a tube and be deployed into the interior of a container. Such a membrane may be produced by means of dip molding, extrusion and blow forming, thermo-forming, and/or any other appropriate polymer processing technique. Appropriate geometric forms of the expandable membrane in the initial un deformed configuration may include, but are not limited to, concentrically arranged longitudinal folds, overlapping folds arranged within a plane of a membrane's cross section, expandable cross sectional shapes such as an expandable star-cross-section, and//or any other appropriate combination of flexible material properties, folding geometries, and/or cross sectional shape as the disclosure is not limited in this fashion.

Regardless of the specific construction, an expandable membrane may have an initial configuration that is sized and shaped to fit at least partially within a correspondingly sized and shaped tube. For example, a maximum inner transverse dimension of a tube and a corresponding maximum outer transverse dimension of an associated expandable membrane in the initial undeformed configuration (e.g. a width, diameter, or other appropriate dimension) may be greater than or equal to 0.5 mm, 1 mm, 2 mm, and/or any other appropriate dimension. Correspondingly, the maximum inner transverse dimension of the tube and corresponding maximum outer transverse dimension of the expandable membrane in the undeformed configuration may be less than or equal to 3 mm, 2 mm, 1 mm, and/or any other appropriate dimension. Combinations of the foregoing are contemplated including, for example, a dimension that is between 0.5 mm and 3 mm. Correspondingly, a maximum longitudinal dimension, such as a length, of a tube and/or an associated expandable membrane in the undeformed configuration may be greater than or equal to 10 mm, 11 mm, 12 mm, and/or any other appropriate dimension. The maximum longitudinal dimension may also be less than or equal to 14 mm, 13 mm, 12 mm, 11 mm, and/or any other appropriate dimension. Combinations of the above are contemplated including, for example, a maximum longitudinal dimension of a tube and/or the expandable membrane in the undeformed configuration that is between or equal to 10 mm and 14 mm. Of course, it should be understood that dimensions both greater than and less than those noted above are also contemplated as the disclosure is not limited to any specific size and/or shape of a tube and associated expandable membrane.

Once an expandable membrane is deployed out of an associated tube, the expandable membrane may expand to any desired shape, longitudinal dimension, and/or transverse dimension in order to pressurize the interior volume of an associated container including a therapeutic composition. In some instances, the expandable membrane may either have sufficient size and/or flexibility in order to contact one or more interior surfaces of the container including surfaces such as a surface located opposite from the associated tube and/or one or more surfaces located to the sides of the tube. However, embodiments in which the expandable membrane does not contact any of the interior surfaces of the container are also contemplated as the disclosure is not so limited.

The frangible barrier separating the reactive substances may be made from any appropriate material and may have any appropriate construction capable of separating the reactants within a reaction chamber while being capable of being broken at a desired time for generating gas. Appropriate types of materials may include, but are not limited to, thin structures of glass, brittle polymers, metallic layered films, or any combination of these three.

To facilitate the use of thin wearable devices, the inventors have recognized the benefits associated with systems including a removeable housing that is used to selectively retain a filling device on an associated drug delivery device. In accordance with some embodiments, the drug delivery system may include a removeable housing that selectively couples to a surface of the drug delivery device that permits the housing to be retained on the drug delivery device in an initial configuration and removed from the drug delivery device after the drug delivery device has been filled with a desired therapeutic composition. In such an embodiment, the filling device may be connected to the housing using an alignment structure and a corresponding connection. As elaborated on below, the alignment structure and connection may help to align a filling needle of the filling device with an associated septum of the drug delivery device and/or the filling device. In either case, the filling needle may extend through a septum of the drug delivery device in the connected configuration for filing purposes and a container including the therapeutic compound may subsequently be displaced to pierce a septum of the container as detailed further herein. After the filling device fills a reservoir in the drug delivery with the therapeutic composition, the housing and attached filling device (and any other parts attached to the housing) may be easily removed and discarded, leaving the delivery device on the subject's body.

Depending on the application, a filling needle may either be initially assembled with either a filling device and/or a drug delivery device. Possible embodiments related to these options are detailed further below.

As noted above in some embodiments, the filling needle may be pre-assembled with a filling device. In such an embodiment, A first portion of the filling needle may extend out of the base such that when the filling device is attached to the drug delivery device, it pierces the septum on the drug delivery device and is in fluid communication with the reservoir of the drug delivery device. Thus, such an arrangement may provide a simple, easy to use method for filling the device with a therapeutic drug. Alternatively, the filling needle may be provided as a separate piece, such as in a retainer clip or other construction, that is initially attached to a portion of the drug delivery device before the filling device is attached. In this arrangement, the first portion of the filling needle may be in fluid communication with the reservoir of the drug delivery prior to connection of the filling device. The filling device may then be subsequently attached to the drug delivery device, and the container septum of the filling device may be aligned with a second end of the filling needle such that the filling needle is configured to pierce the septum of the container when the filling device is activated. After activation, the filling needle, and any associated connections such as a retainer clip, may remain attached to the filling device so that it may be removed from the drug delivery device with the filling device. By having a separate filling needle located on the drug delivery device, rather than the filling device, this may help to ensure that the filling needle will not pierce the container septum during storage. Of course, while two possible arrangements for the filling needle of a drug delivery to system have been described above, it should be understood that the current disclosure is not limited to any particular arrangement of these features as the disclosure is not limited in this fashion.

It should be noted that the filling needle may be any hollow tubular structure with a closed cross section with a channel that extends through a length of the needle such that the two end portions of the needle may be in fluid communication with one another. For example, a needle may be used to place a container within a filling device and a reservoir of the drug delivery device in fluid communication with each other through the channel extending through the needle. Additionally, in some embodiments, either one, or both ends of a needle may include sharp pointed tips that are configured to pierce other structures such as a septum and/or tissue.

As noted above, in some embodiments, a filling device includes a container (e.g., (vial or cartridge) containing a volume of a therapeutic component disposed in an interior volume of the container. For purposes of this application, the terms vial, cartridge, and container may be used interchangeably as the disclosure is not limited to any specific construction of a container that is configured to contain a volume of therapeutic composition. Additionally, a container may be configured to hold any appropriate volume of a therapeutic composition for a desired application. For example, a container may hold a volume of therapeutic component ranging from 2 mL to 10 mL, 2 mL to 20 mL, and/or any other appropriate volume. A container may also include a maximum outer transverse dimension, such as a width or diameter, that is between or equal to 16 mm and 47 mm as well as a maximum longitudinal dimension, such as an overall length, that is between or equal to 35 mm to 100 mm in overall length. Of course, while specific dimensions and volumes are given above, it should be understood that any appropriate volume and/or dimension may be used for a container including volumes and/or dimensions that are greater than or less than those noted above as the disclosure is not so limited.

As used herein, the term "therapeutic composition" (also referred to as a "drug", "therapeutic agent", and/or therapeutic compound) refers to an agent that is administered to a subject to treat a disease, disorder, or other clinically recognized condition, or for prophylactic purposes, and has a clinically significant effect on the body of the subject to treat, prevent, and/or diagnose the disease, disorder, or condition. The therapeutic composition may be delivered to a subject in a quantity greater than a trace amount to affect a therapeutic response in the subject. In some embodiments, therapeutic compositions can include, but are not limited to, any synthetic or naturally-occurring compound or composition of matter which, when administered to a subject (e.g., a human or nonhuman animal), induces a desired pharmacologic, immunogenic, and/or physiologic effect by local and/or systemic action. A therapeutic composition may include vitamins, nutrients, tracers (magnetic, radioisotope, luminescent, and/or fluorescent); fluorescent dyes; and/or any other appropriate therapeutic composition that might be desired to be delivered to a subject. Accordingly, it should be understood that the therapeutic compositions described herein are not limited to any particular type of therapeutic composition.

Depending on specific therapeutic composition to be provided to a subject, a filling device may be filled with therapeutic compositions with a range of different viscosities. For example, a viscosity of the therapeutic composition may be greater than or equal to 1 cPoise, 5 cPoise, 10 cPoise, 20 cPoise, 30 cPoise, and/or any other appropriate viscosity. Correspondingly, the viscosity of the therapeutic composition may be less than or equal to 50 cPoise, 40 cPoise, 30 cPoise, 20 cPoise, 10 cPoise, and/or any other appropriate viscosity. Combinations of the foregoing ranges are contemplated including, for example, a viscosity of a therapeutic composition that is between or equal to 1 cPoise and 50 cPoise. Of course viscosities both greater than and less than those noted above are also contemplated as the disclosure is not so limited.

While a majority of the embodiments described herein are directed to filling devices for filling the reservoir of a drug delivery device, it should be appreciated that the devices described above should not be limited to only being used as filling devices. For example, the devices described herein may be used as a standalone device to dispense a therapeutic composition into any desired location and/or structure including directly into a patient (e.g., autoinjectors). Accordingly, it should be appreciated that the drive system, structures, and device described herein may be used in any number of different applications.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 is a perspective view of a drug delivery system according to one embodiment. As shown in FIG. 1, the drug delivery system 100 includes a drug delivery device 102, a housing 104 coupled to the drug delivery device, a cannula insertion system 106, and a filling device 108. The drug delivery device 102 may be an on-body drug delivery system ("OBDDS") or any type of device that accepts a therapeutic composition from a filling device. As detailed further below, the filling device 108 may be aseptically coupled with the drug delivery device 102 to transfer a therapeutic composition from the filling device into a reservoir of the drug delivery device. After the reservoir is filled, a cannula insertion system 106 may deploy a cannula of the drug delivery device into a patient. The cannula insertion system may be any appropriate type of cannula insertion device that inserts a cannula into a patient to deliver the therapeutic composition including, for example, a needle insertion based system. However, regardless of the specific arrangement of the drug delivery device, filling device, and other associated component, the filling device and other associated components may be removable from the drug delivery device attached to a subject's body after dispensing a desired therapeutic composition into a reservoir of the drug delivery device. Accordingly, the depicted system may help to enable the use of a low profile and small footprint drug delivery device on the subject's body.

Figure 2:
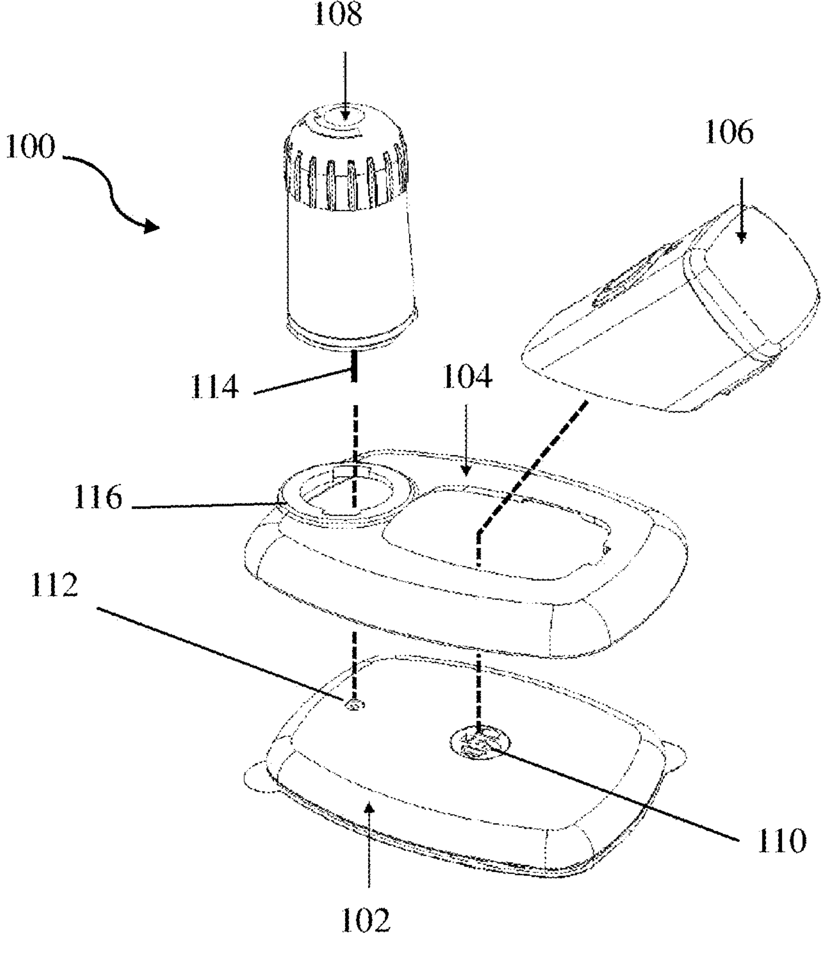
FIG. 2 is a schematic perspective exploded view of a drug delivery system according to one embodiment.

FIG. 2 is an exploded perspective view of the embodiment in FIG. 1. As shown in FIG. 2, the drug delivery device may include a cannula insertion device lock 110, such as the depicted recesses which may selectively engage with mechanically interlocking features on the cannula insertion system 106, not depicted. However, regardless of the specific connection between the cannula insertion device and the drug delivery device 102, the cannula insertion device may be used to deploy a cannula of the drug delivery device into the tissue of a subject. The drug delivery device 102 may also include a septum 112 that is associated with and seals at least a portion of a reservoir of the drug delivery device that is configured to contain a desired therapeutic composition for dispensing into the tissue of a subject through the above-noted cannula.

In some embodiments, a housing 104 may be selectively coupled to the drug delivery device 102. The housing 102 may include any removable connection that attaches the housing to the filling device 108. In some instances, the cannula insertion device 106 connected to the housing such that removing the housing from the drug delivery device removes the cannula insertion device as well. In the depicted embodiment, the housing is connected to the drug delivery device via the cannula insertion device lock 110 that is used to selectively maintain the cannula insertion device attached to the drug delivery device. However, instances in which separate connections between the housing and the drug delivery device are used are also contemplated. As shown in figure, the housing 104 may include openings and alignment structures that are configured to accept the cannula insertion device 106 and the filling device 108 such that the cannula insertion device and filling device are positioned their respective desired location and orientation relative to the underlying drug delivery device. For example, the housing may have a first alignment structure 116 that engages with a corresponding alignment structure on the filling device 108, not depicted, such that when the filling device is attached to the housing a filling needle 114 disposed on a bottom portion of the filling device oriented towards the drug delivery device is aligned with and oriented towards the septum 112 on the drug delivery device 102. Thus, when the filling device is connected to the drug delivery device, the filling needle may pierce the septum 112 of the drug delivery device such that the filling device is in fluid communication with the reservoir through the filling needle. The filling device 108 may been deliver the therapeutic composition into the reservoir of the drug delivery device 102 through the filling needle 114 using any of the methods disclosed herein.

Figure 3:
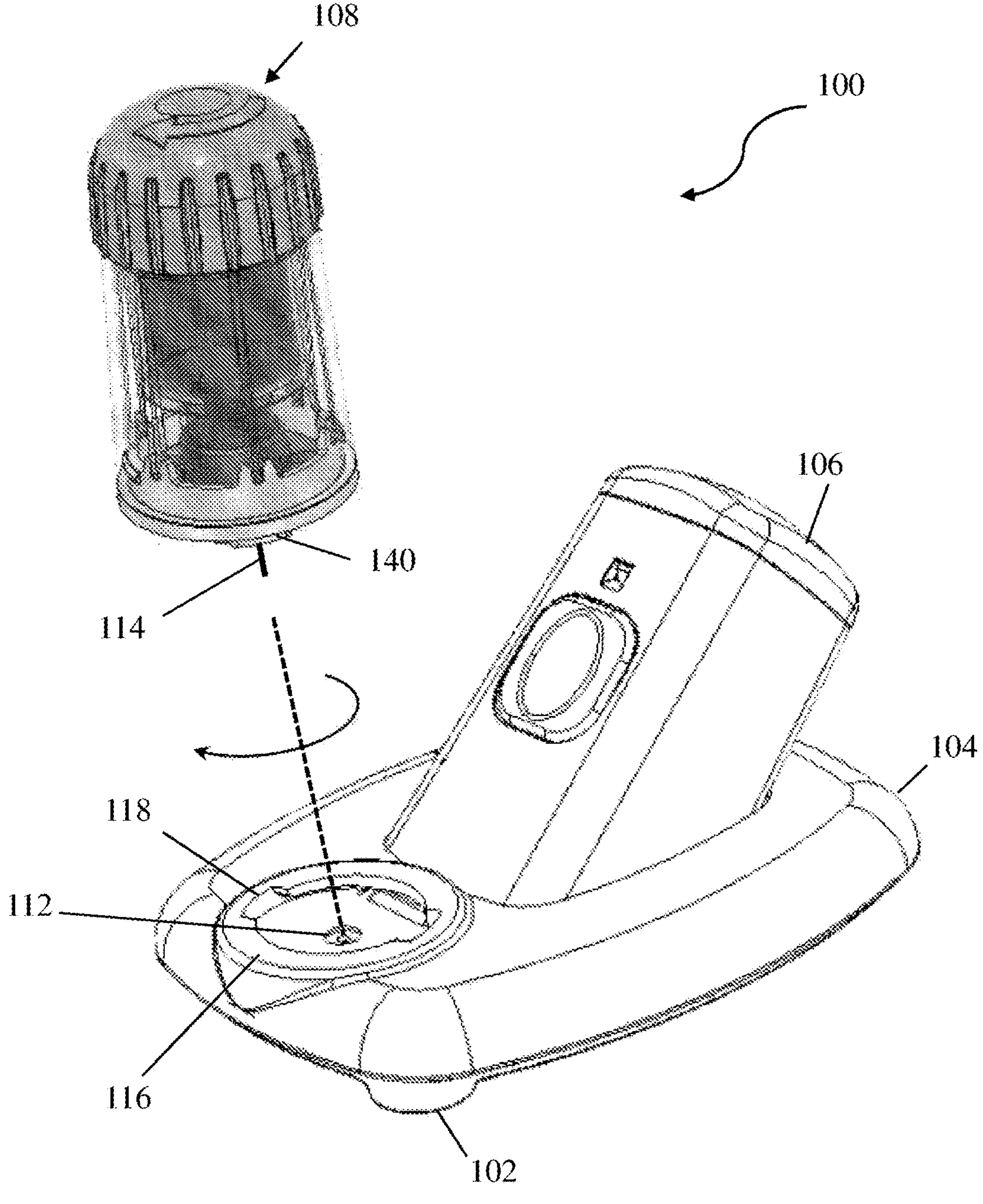
FIG. 3 is a schematic perspective view of a filling device being aligned with and attached to a drug delivery device according to one embodiment.

FIG. 3 illustrates one possible embodiment of an attachment between a filling device 108 and a drug delivery device 102. Here, the housing 104 and cannula insertion device 106 are already attached to the drug delivery device 102 in an initial undeployed configuration. While the alignment structure and the filling device and the corresponding alignment structure(s) on the housing and/or drug delivery device may have any appropriate corresponding construction to provide the desired alignment, in some embodiments, the alignment structure 116 on the housing may be round opening with notches 118 extending radially outward along a portion of the openings periphery. The notches may be sized and shaped to accept complementary shaped projection including winged tabs 140 disposed on a portion of the filling device 108 oriented towards the drug delivery device in the attached configuration. The winged tabs 140 may be positioned in a location near the filling needle 114 such that when the winged tabs 140 engage the notches 118, the filling needle 114 is aligned with the septum 112 of the drug delivery device 102. To attach the filling device, a user may insert the winged tabs 140 into the notches 118 in the alignment structure 116 and then rotate the filling device 108 along its longitudinal axis to secure the tabs under a ledge of the alignment structure 116 thus locking the filling device into position. Again, once locked in the attached and aligned configuration, the filling needle 114 may be inserted into the septum 112. The filling device 108 may be in fluid communication with the reservoir of the drug delivery device 102 and the needle may be oriented towards a corresponding septum of the filling device as elaborated on below.

It should be appreciated that the filling device 108 and housing 102 may include other types of alignment and connections as the disclosure is not limited to the specific way in which the filling device and housing are aligned and attached to one another. For example, a threaded connection, snap fit, press fit, latches, or other appropriate connections may be used to selectively retain the filling device on the housing. Additionally, any appropriate construction capable of aligning a filling needle with either a septum of the filling device and/or the drug delivery device may be used. For instance, appropriate alignment structures may include, but are not limited to, correspondingly shaped projections and holes, grooves and slots, detents, and/or any other appropriate construction as the disclosure is not limited in this fashion. Further, while the filling device is depicted as being attached to the removable housing, embodiments in which a filling device attaches directly to a drug delivery device are also contemplated.

Figure 4:
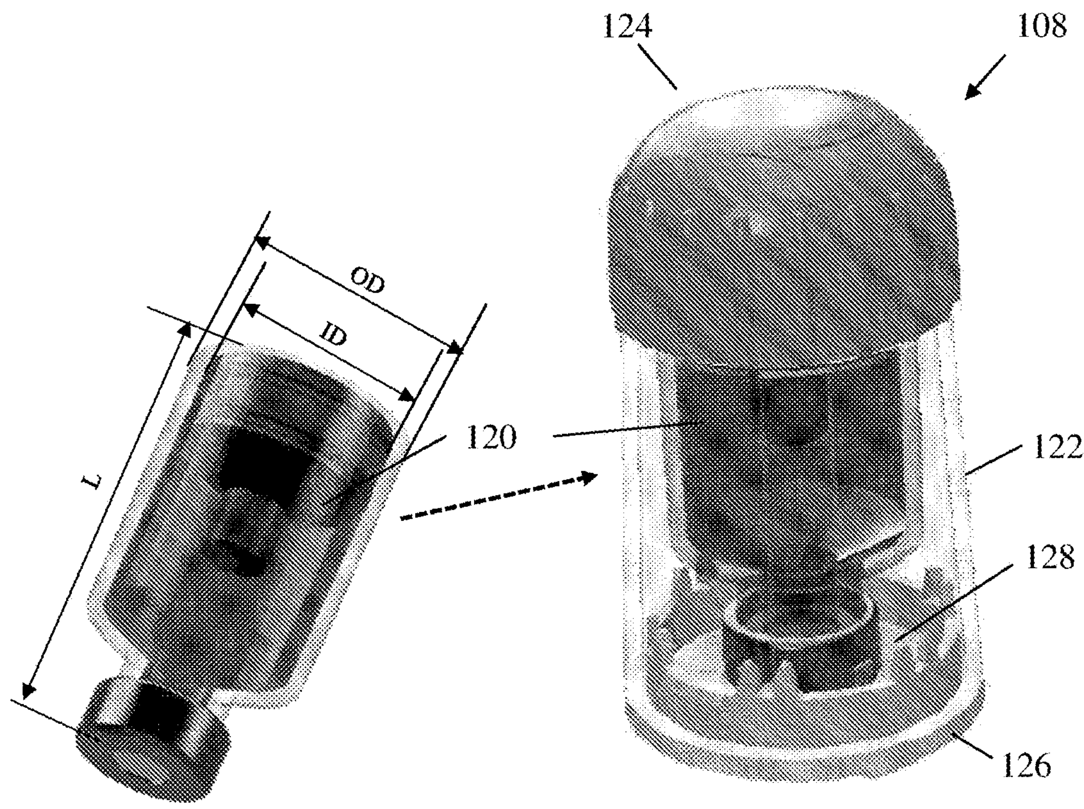
FIG. 4 is a schematic perspective view of a filling device according to one embodiment.
Figure 5:
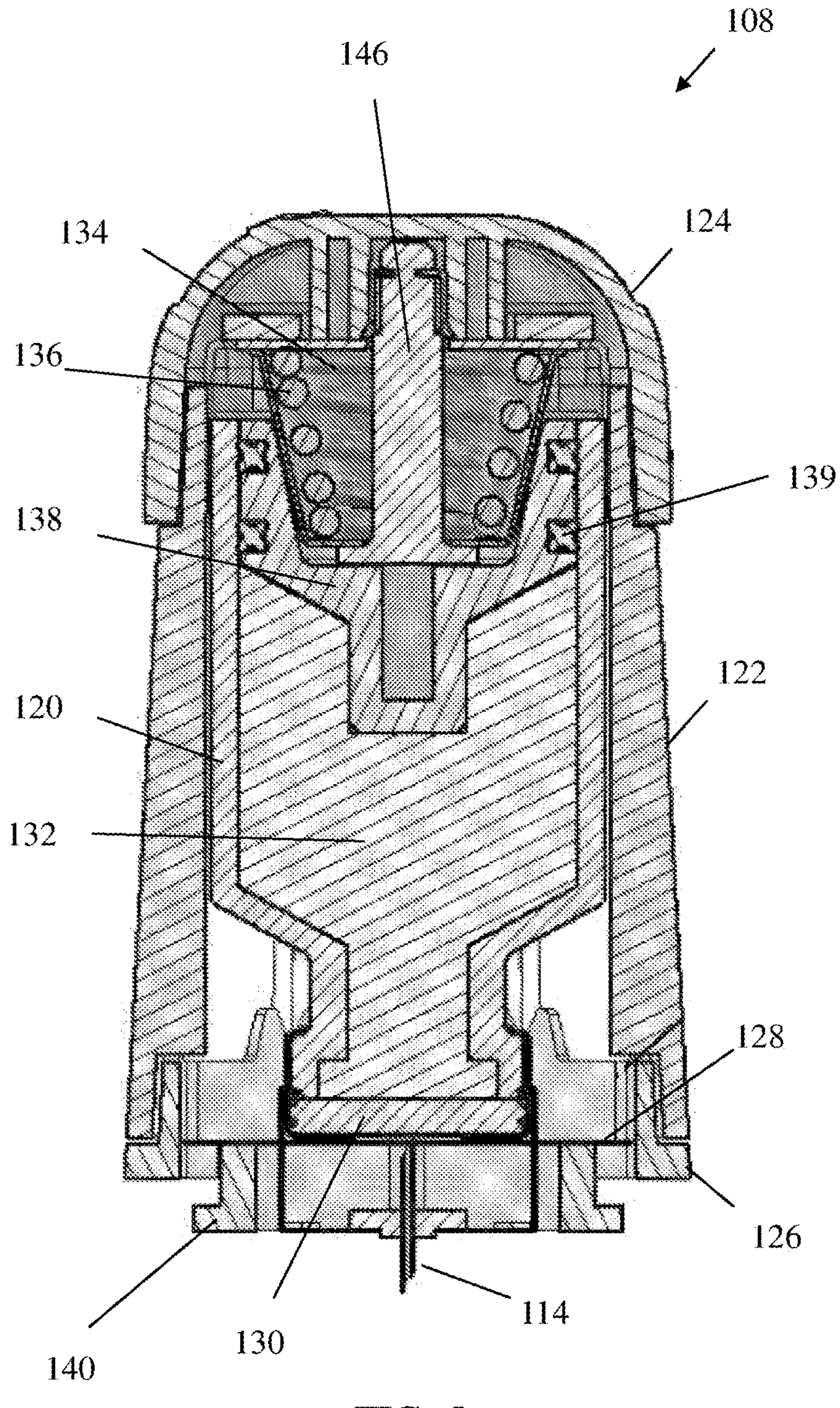
FIG. 5 is a schematic cross-sectional view of a filling device in an unactuated configuration according to one embodiment.
Figure 6:
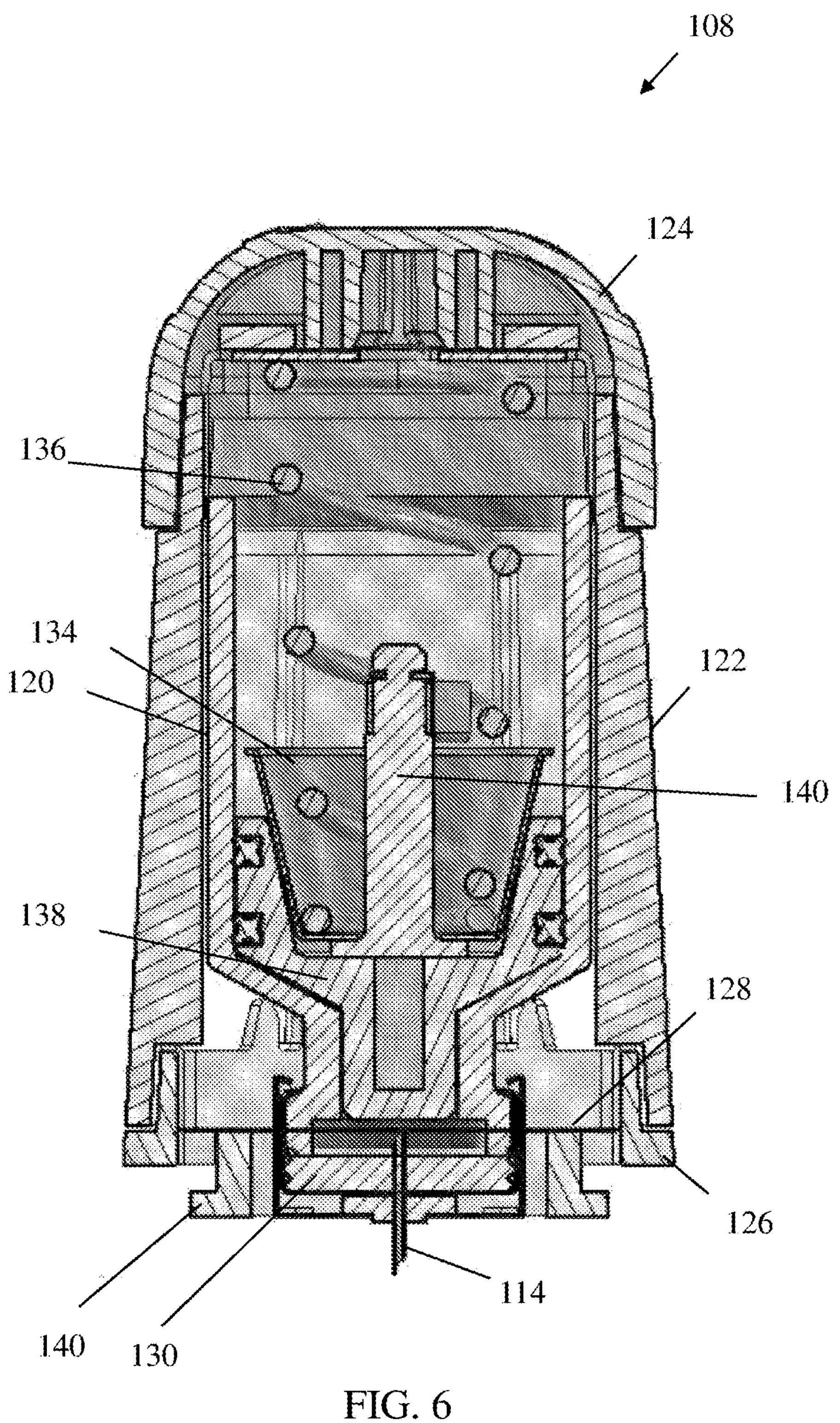
FIG. 6 is a schematic cross-sectional view of a filling device in an actuated configuration according to one embodiment.

A filling device 108 is shown in FIGS. 4-6 according to some embodiments. The filling device includes a filling device housing having a main enclosure 122, a cap 124, and base 126. The filling device housing is sized and shaped to receive and securely hold a container 120 containing a therapeutic composition. The filling device housing may be cylindrical in shape or any other appropriate shape that is configured to appropriately contain and hold the container. The container 120 may be securely positioned within the main enclosure 122 between the cap 124 and the base 126. In some embodiments, the main enclosure 122 may be manufactured from a rigid, transparent material such that the container 120 may be seen through the main enclosure to visually verify its volume status and whether it is full or empty of a therapeutic composition. Non-transparent materials may also be used; in such cases the filling device may include a separate volume gauge indication to verify the volume status of the container. The main enclosure 122 may include an exterior label (not shown) to display applicable data regarding the therapeutic composition (e.g., branding, bar coding, date of manufacture, expiration, and indications for use). Labeling techniques may include standard decorative printing methods such as shrink-wrap thin films secured to the filling device at the final stages of packaging.

To avoid unwanted movement of a container within the filling device housing 108 prior to actuation, in some embodiments, the container may be held in place by a membrane 128, or other restraint that may support loads up to a threshold force while preventing movement beyond a threshold displacement of the container. Accordingly, when a load greater than the threshold force is applied to the container, the associated restraint, such as the depicted membrane, may either break or deform allowing the container to move in a desired direction. The flexible membrane, restraining tabs, or other appropriate restraint may be configured to support any desired threshold force. However, in some embodiments, the restraint may be configured to support loads up to a threshold force that is between or equal to 2 times and 4 times a weight of the container including the therapeutic composition.

As noted previously, the filling device housing may be sized and shaped to accept any desired container having any appropriate inner transverse dimension ID (e.g. inner diameter or width), outer transverse dimension OD (e.g. outer diameter or width), and/or longitudinal dimension L (e.g. length). Accordingly, the filling device may be configured to dispense any appropriate amount of therapeutic composition depending on the desired application.

According to some embodiments, the container 120 is not physically exposed or touched once it is inserted into an interior of the filling device 108. As such, the therapeutic composition contained in the container 120 may remain sterile, sealed, and uncompromised until the filling device is actuated to dispense the therapeutic composition from the container to a desired location (e.g., injected into a subject or drug delivery device).

FIG. 5 is a cross-sectional view of a filling device 108 according to some embodiments. As shown in FIG. 5, the main enclosure 122 attaches to the cap 124 at one end portion and to the base 126 at a second end portion to create an interior volume disposed there between. In some embodiments, the cap is rotatably, or otherwise movably, attached to the main enclosure of the filling device housing such that the cap may be displaced relative to the housing to actuate the device as detailed further below. The interior volume of the filling device 108 may be sized and shaped to contain a container 120 and an associated drive system 134 configured to axially displace the container 120 to dispense the therapeutic composition when the filling device is activated. The main enclosure 122 includes an elongated wall that may be cylindrical in shape and have an inner diameter that closely matches the outer diameter of the container 120 while permitting a slip fit of the vial within the interior volume in a desired direction of movement. However, it should be understood that other arrangements where other guide structures such as struts are positioned proximate to the container to maintain the vial in a desired position and orientation above prior to and during actuation also contemplated.

In some embodiments, the main enclosure 122 may be rigidly attached to the base 126 to create a sealed connection (e.g., a snap fit, threaded connection, weld, or any other appropriate connection) after the container 120 and drive system 134 are assembled within the filling device. The wall of the main enclosure at an end connected to the base may have a complementary shape to accept a top portion of the base. For example, in some embodiments, the wall of the main enclosure 122 may have an internal ledge that rests on a top portion of the base 126. The wall of the main enclosure 122 may extend over the top portion of the base 126 and along the outside of the base until it rests on an outer ledge of the base 126. However, any appropriately shaped base and main enclosure interface and any appropriate type of connection may be used as the disclosure is not limited in this fashion.

As noted above, in some embodiments, the cap 124 is rotatably attached to the main enclosure 122 such that the cap may rotate relative the main enclosure about a longitudinal axis of the filling device. The cap may include external ribs or an otherwise rough and/or easily gripped outer surface to permit the cap to be easily rotated (see FIG. 4). As detailed further below, rotation of the cap may function as a trigger to actuate the filling device. However, embodiments in which a different trigger such as a mechanical button, slide, latch, lever, electronic button, and/or any other appropriate trigger are used are also contemplated as the disclosure is not so limited.

As discussed above in regards to FIG. 3, in some embodiments, a bottom portion of the base 126 may include a filling needle 114, which in the depicted embodiment is positioned along the longitudinal axis of the filling device though other orientations and/or positions are also possible. As noted above, the needle 114 may be positioned such that when the filling device is attached to the drug delivery device, the filling needle is aligned with and pierces a septum of a drug delivery device such that the filling needle is in fluid communication with a reservoir of the drug delivery device. Thus, in some embodiments, a first end of the filling needle includes a sharp end that extends outwards away from an adjacent portion of the filling device. The filling needle 114 may also include a second sharp end that is configured to pierce an associated septum. This second sharp end may be oriented towards a septum 130 of the container 120. The septum 130 seals the therapeutic composition 132 in the container 120 once the composition is manufactured and deposited into the container. When the drive system 134 is activated, it axially displaces the container 120 toward the filling needle 114 from an initial unactuated configuration where the septum is distanced from the filling needle and an actuated configuration where the filling needle 114 is pierced through the septum 130 and is in fluid communication with the therapeutic composition 132 inside the container 120. Thus, the therapeutic composition in the container may be in fluid communication with the reservoir of the drug delivery device through the filling needle, and the therapeutic composition 132 may flow from the container through the filling needle 114 into the reservoir once a pressure is applied to an interior of the container as expanded on below. Additionally, although a single filling needle is shown, it should be appreciated that one or more filling needles may be used.

In some embodiments, the base 126 includes a restraint 128, such as the depicted membrane that extends across an internal cross section of the interior volume of the filling device housing, such that the container is maintained in a desired orientation and/or location prior to actuation as previously discussed by supporting a weight of the vial containing the therapeutic composition when the filling device is unactuated. Thus, the restraint may help to prevent unintentional piercing of the container's septum 130 by the filling needle 114 prior to actuation of the drive system 134. However, once actuated, the drive force applied to the vial by the drive system may axially the container 120 toward the filling needle 114 causing the septum 130 to press against the restraint with sufficient force to bend or fracture the restraint so that the container may be displaced to a configuration where the filling needle pierces through the septum 130, see FIG. 6.

In accordance with some embodiments, the container 120 includes a piston 138 at a second portion of the container opposite from a first portion of the device including the associated septum 130. The piston 138 may be shaped to effectively seal the therapeutic composition 132 in the container at the second portion while permitting movement of the piston within an interior volume of the container. For example, the piston 138 may have a first outer perimeter sized to fit tightly within the inner diameter of the container. The first outer diameter may extend along a length of the container creating a longitudinal border between the piston and the container. One or more slidable seals 139, such as O-rings having x-shaped cross sections, circular cross sections, and/or any other appropriate sliding seal may be positioned between an interior surface of the container and the piston In some embodiments, the piston 138 has a shape that compliments a shape of an interior portion of the container such that substantially all of the therapeutic composition contained within the container may be displaced out of the container by the piston. For example, in the depicted figure, the piston has shoulders and a neck portion that are shaped to compliment a shape of the necked down region of the container proximate to the septum 130. However, regardless of the piston shape, the drive system may be disposed against, rigidly attached to, or otherwise associated with the piston to apply a desired driving force to the piston. For instance, in the depicted embodiment of FIGS. 5 and 6, a portion of the piston 138 oriented towards the drive system 134 may be shaped to receive a portion the drive system. Specifically, as shown in the figure, the piston may include a recess that is sized and shaped to receive a portion of the of the drive system which may be a truncated cone and corresponding recess in some embodiments as shown in the figure. However, any appropriate type of arrangement of the drive system and piston may be used as the disclosure is not so limited.

In some embodiments, when the drive system 134 is actuated, the drive system may apply a force to an adjacent portion of the container 120, which in FIGS. 5 and 6 corresponds to the piston 138. Due to the container being sealed and mostly filled with an incompressible liquid, this results in the container being displaced toward the filling needle 114, causing the filling needle to pierce the septum 130. Once the filling needle pierces the septum, the piston 138 is displaced relative to the container causing the interior volume of the container to become pressurized which in turn causes the therapeutic composition 132 to be flow out of the container through the filling needle. The drive system 143 exerts sufficient force to move the therapeutic composition through the filling needle at a desired flow rate. This is best seen in FIG. 6 where a configuration of the filling device after the drive system 143 has been actuated is depicted. As shown in the figure, the drive system 134 has axially displaced the container toward the filling needle 114 and the filling needle has pierced the septum 130 and extended into the container. The drive system 143 has also axially displaced the piston 138 towards the septum 130, dispensing the therapeutic composition 132 through the filling needle 114.

The transfer time, measured from when the time the drive system 143 is actuated to the time when the drug delivery has been filled, may vary based on the total volume and viscosity of the therapeutic composition 132. However, appropriate times for dispensing a therapeutic from a device may be between or equal to 10 seconds and 2 minutes though time periods both greater and less than those noted above are also possible.

Figures 7A, 7B:
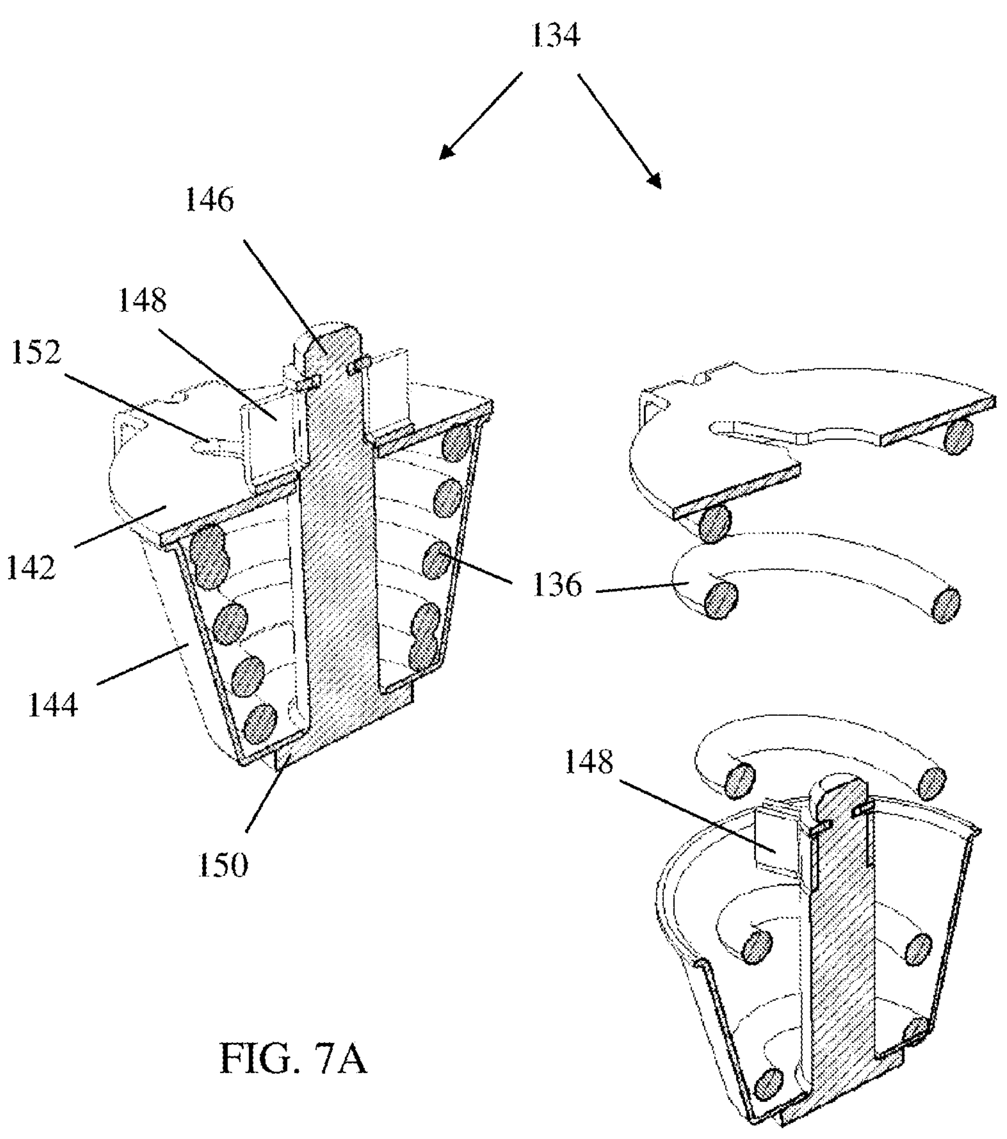
FIG. 7A is a schematic perspective cross-sectional view of a drive system in an unactuated configuration of a filling device according to one embodiment.
FIG. 7B is an exploded cross-sectional view of the drive system in an actuated configuration of FIG. 7A.

As noted previously, the currently disclosed devices may handle therapeutic compositions with volumes and/or viscosities that are associated with relatively large initial actuation forces. However, when stored for long durations, these large initial forces may result in creep of the drive system of a device which may result in unwanted forces and/or displacements being applied to the containers contained within a device. In instances where large enough creep is experienced, this could result in the septum of an associated container being unintendedly pierced by a needle prior to actuation of a device. FIGS. 7A-7B illustrate a drive system 134 that may be included in a filling device 108 to address the above noted issues according to one embodiment. FIG. 7A shows the drive system in a harnessed or unactuated configuration and FIG. 7B shows the drive system in a fully released or actuated configuration. In the harnessed configuration, the drive system restrains a potential energy source, such as a spring. When the drive system is actuated (e.g. by rotating the cap 124 as described above), a lock of the drive system is actuated from a locked to an unlocked configuration to allow the drive system to convert the potential energy to kinetic energy sufficient to drive the piston 138 to axially displace the container 120 and dispense therapeutic composition 132 through the filling needle. In some embodiments, the drive system 134 includes first and second portions of a drive housing that may be selectively coupled to one another by a lock to restrain the mechanical potential energy source between them.

In the depicted embodiment, a thrust plate 142 and a loading cup 144 form an interior volume in the initial unactuated configuration with a spring 136 or other compressed elastic structure disposed in the interior volume between the thrust plate and loading cup in a compressed configuration. The thrust plate and loading cup are restrained in this configuration by a lock 146 that holds the thrust plate 142 and the loading cup 144 in the initial retracted configuration. While any lock may be used, the depicted lock includes a first lock portion with a shaft extending from the loading cup, or other portion of the drive housing, through a slot 152 formed in the thrust plate 142, or other portion of the drive housing. In some embodiments, a first end portion of the shaft may be rotatable attached to the loading cup, such as by the head 150 disposed against an exterior surface of the loading cup with the shaft extending through a hole formed in the loading cup. However, other rotatable attachments are also possible. In either case, the shaft may apply a restraining force to the loading cup while still permitting rotation of the shaft relative to both portions of the drive housing. The shaft and associated portion of the loading cup may be made from appropriately still materials and be sized appropriately to avoid creep under the loads applied by the drive system prior to actuation. Again, this may avoid applying unintended displacements and forces to a container prior to actuation. To exert the noted restraining force to the loading cup, or other portion of a drive system, a second end portion of the shaft opposite from the attachment to the loading cup may include a mechanically interfering structure, such as the depicted key tabs on release key 148, that are configured to prevent movement of the shaft relative to the thrust plate in a first orientation and permit movement of the shaft relative to the thrust plate in a second orientation once the shaft has been rotated relative to the drive housing. Thus, the lock 146 restrains the loading cup relative to the thrust plate until the drive system is actuated. For instance, the previously illustrated rotatable cap may rotate the key tabs until they are aligned with the associated slot at which point the drive system may be unlocked. However, regardless of the specific lock, when the drive system is actuated, the lock 146 may release the thrust plate and the spring 136 may exert sufficient force to axially displace the loading cup 144 (and therefore the container and piston 138) away from the thrust plate 142, as shown in FIG. 7B.

Figures 8A, 8B:
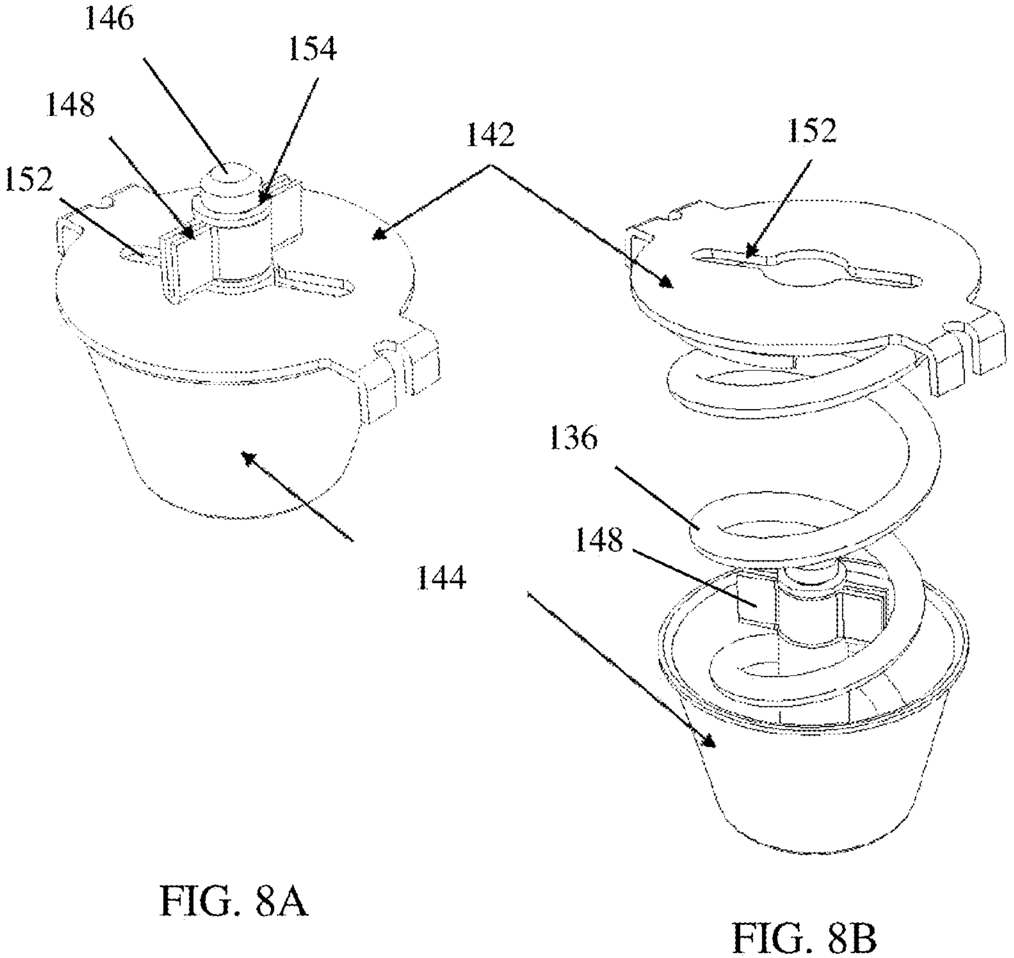
FIG. 8A is a schematic perspective view of a drive system in an unactuated configuration of a filling device according to one embodiment.
FIG. 8B is an exploded perspective view of the drive system in an actuated configuration of FIG. 8A.

The slot and mechanical key tabs on release key 148 are described further with reference to FIGS. 8A-8B. In the depicted embodiment, the release key 148 may be operative connected to the cap 124 of a filling device (see FIGS. 4-5) such that rotating the cap 124 also rotates the tabs on the release key 148. Before actuation, the tabs rest against a top surface of the thrust plate, as shown in FIG. 8A. The key tabs may be held onto the lock 146 by a retaining ring 154 held in a ridge in the lock's shaft. However, any appropriate method of attaching the tabs, or other structure, to the shaft may be used including, but not limited to, integral formation, welding, and threaded fasteners. In either case, when the cap 124 is rotated from a first initial orientation to a second orientation, the key tabs, or other mechanically interfering structure, may become aligned with the slot 152 such that the key tabs are able to pass through the slot permitting the shaft and operatively coupled loading cup, or other portion of the drive system, to be displace relative to the thrust plate allowing the spring to decompress, as shown in FIG. 8B.

While a particular method and construction for restraining two portions of a drive housing relative to one another to contain a compressed mechanical potential energy source has been depicted in the above figures, it should be understood that other appropriate locks and constructions of the drive system may also be used. For example, linearly actuated locks, locks actuated by rotation about other axes, and/or different types of locks such as latches, threaded connections, interference pins, and/or any other appropriate type of lock may be used as the disclosure is not limited in this fashion.

Figure 9:
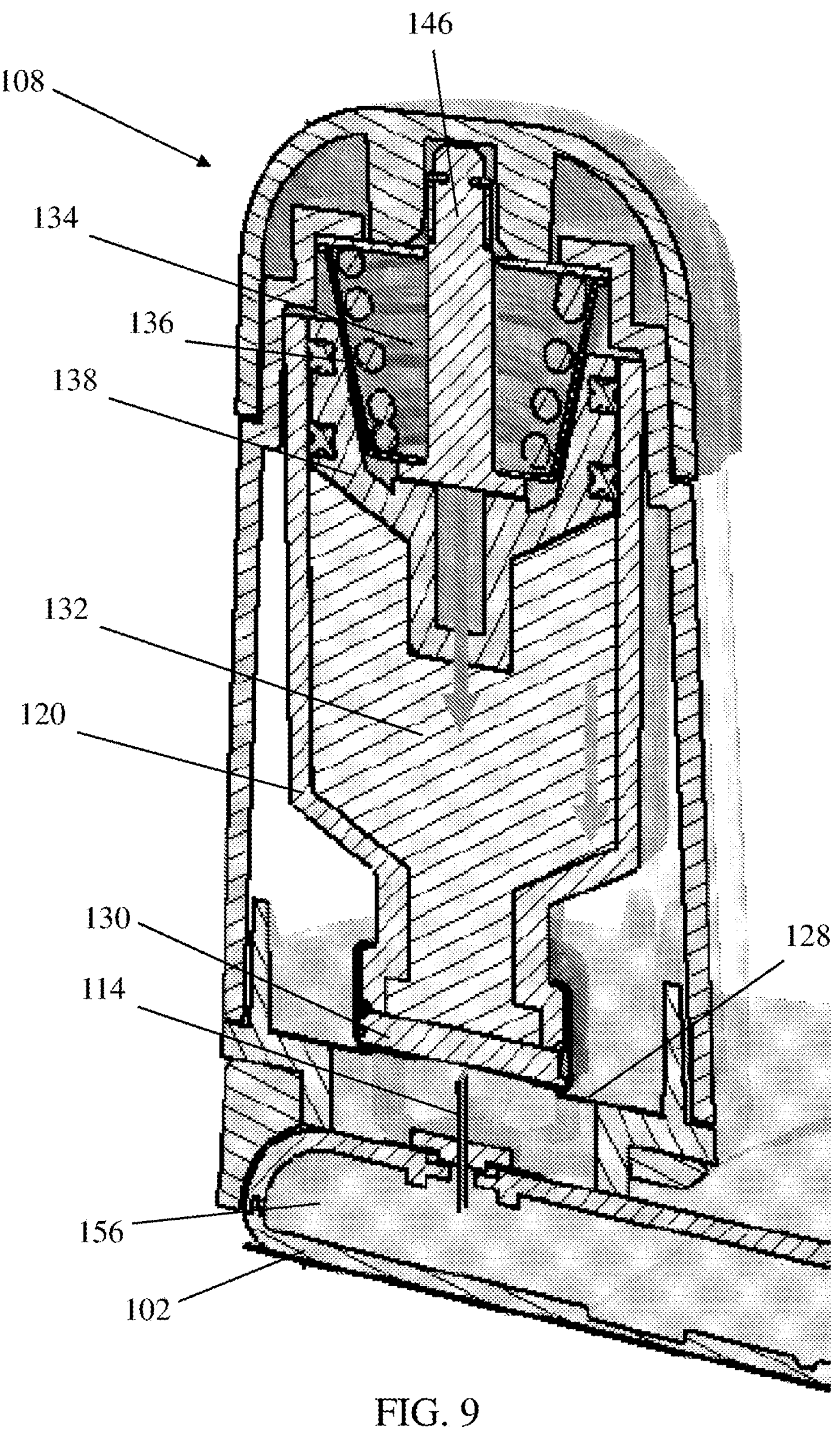
FIG. 9 is a perspective cross-sectional view of a drug delivery system prior to actuation according to one embodiment.
Figure 10:
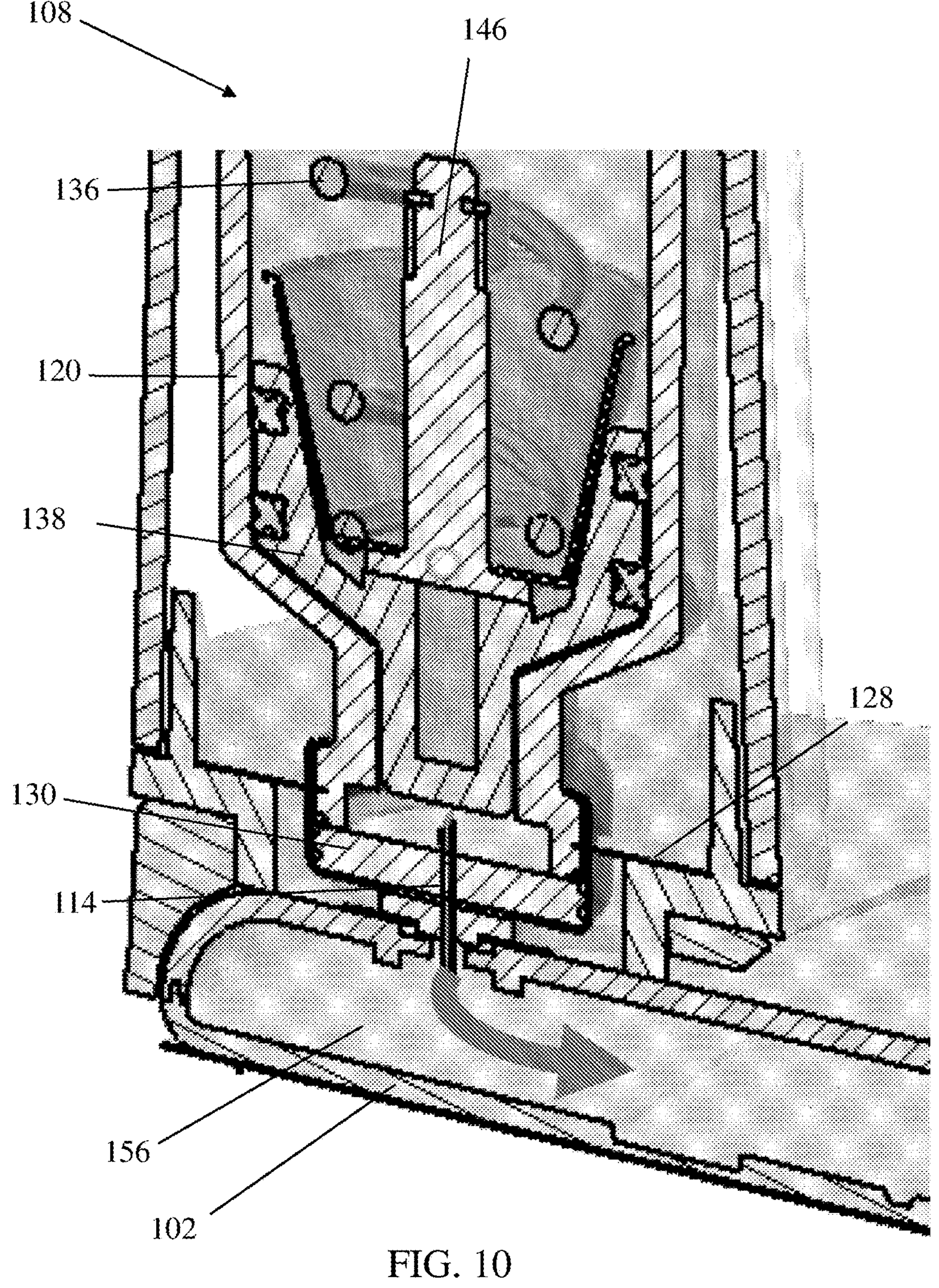
FIG. 10 is the drug delivery device of FIG. 9 after actuation.

FIGS. 9-10 are cross-sectional perspective views of a filling device 108 connected to a drug delivery device 102 according to one embodiment. In FIG. 9, the filling device has not yet been activated and the container 120 contains a full volume of the therapeutic composition 132. The septum 130 rests on the restraint 128, which in the depicted embodiment is a membrane, preventing the filling needle from puncturing the container's septum. The filling needle 114 has pierced a septum of the drug delivery device and is in fluid connection with the reservoir 156 of the drug delivery device 102. The drive system 134 contains the compressed spring 136 in the initial unactuated configuration using a lock 146 as described above. In FIG. the filling device 108 has been actuated. The drive system 134 is in a fully released state and the container has been axially displaced toward the filling needle, bending or fracturing the restraint 128 to permit the container to be displaced towards the filling needle. The filling needle has also pierced the septum 130 of the container, placing the container 120 in fluid communication with the reservoir 156 through the filling needle. The drive system has axially displaced the piston 138 towards the first end of the container and the therapeutic composition 132 has been dispensed through the filling needle into the reservoir 156 in a direction shown by the arrow. The drug delivery device 102 is now ready to be used for on-body therapy use (i.e., injection).

Figure 11:
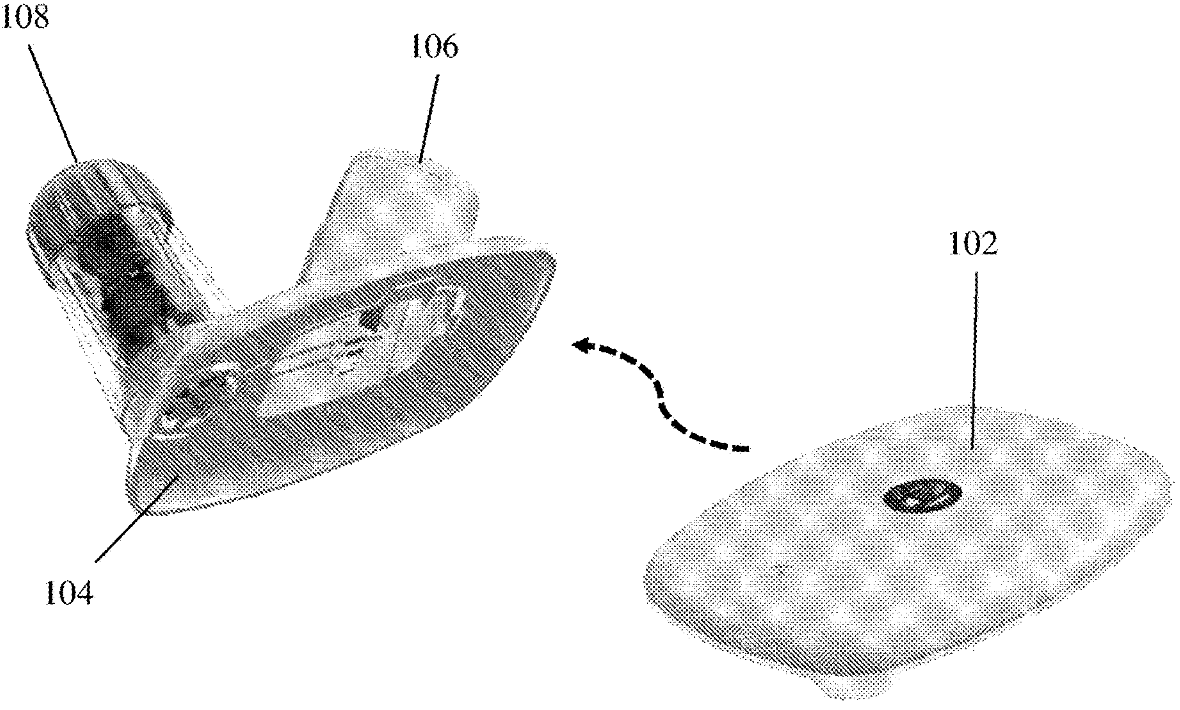
FIG. 11 is an exploded perspective view of a removable shroud housing with an attached filling device and cannula deployment module attached thereto that are detached from an associated drug delivery device according to one embodiment.

In accordance with some embodiments, the housing 104, cannula insertion system 106, and filling device 108 may be removed from the drug delivery device 102 and discarded after the device is used for on-body therapy, as shown in FIG. 11. In some embodiments, the filling device 108 and injection system 106 are attached to the housing 104 and all three components may be easily removed as one piece from the drug delivery device. The drug delivery device may remain on the patient for the duration of therapeutic delivery. Depending on the embodiment, this selective connection may be provided by a connection that is released such as when the cannula insertion device is actuated (see above description), the filling device is actuated, and/or any other appropriate trigger is actuated to release an attachment and actuate a desired functionality. Additionally, more simple releasable connections such as actuatable locks, latches, snap connections, threaded fasteners, and/or any other selectively detachable connecter may be used as the disclosure is not limited to how the housing, filling device, and/or cannula insertion system are removed from the drug delivery device.

Figure 12:
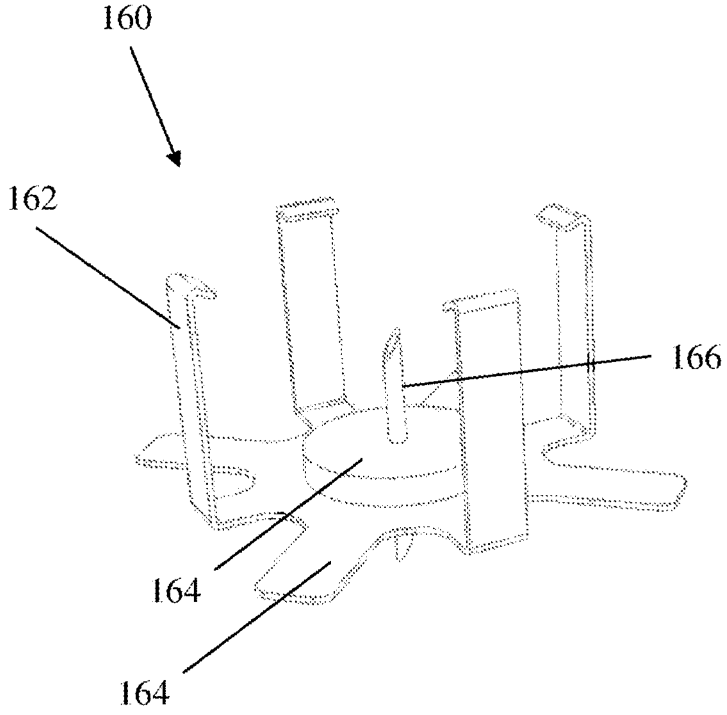
FIG. 12 is a schematic perspective view of a modular retaining clip and piercing needle according to one embodiment.

In the above embodiments shown in the figures, a filling needle integrated with a filling device is shown. However, an alternative embodiment of a drug delivery system 100 is described with reference to FIGS. 12-14. In accordance with some embodiments, a drug delivery system includes a separate retainer clip 160 including a filling needle 166. The filling needle 166 is positioned on the retainer clip in a hub 164 which seals the outer diameter of the filling needle. The hub may be a round disc aligned with the filling needle. The filling needle 166 includes a first end to pierce the septum on the drug delivery device (see FIG. 3) and a second end to pierce a septum of a container containing a therapeutic composition, placing the container in fluid communication with a reservoir in the drug delivery device through the needle.

Figure 13A:
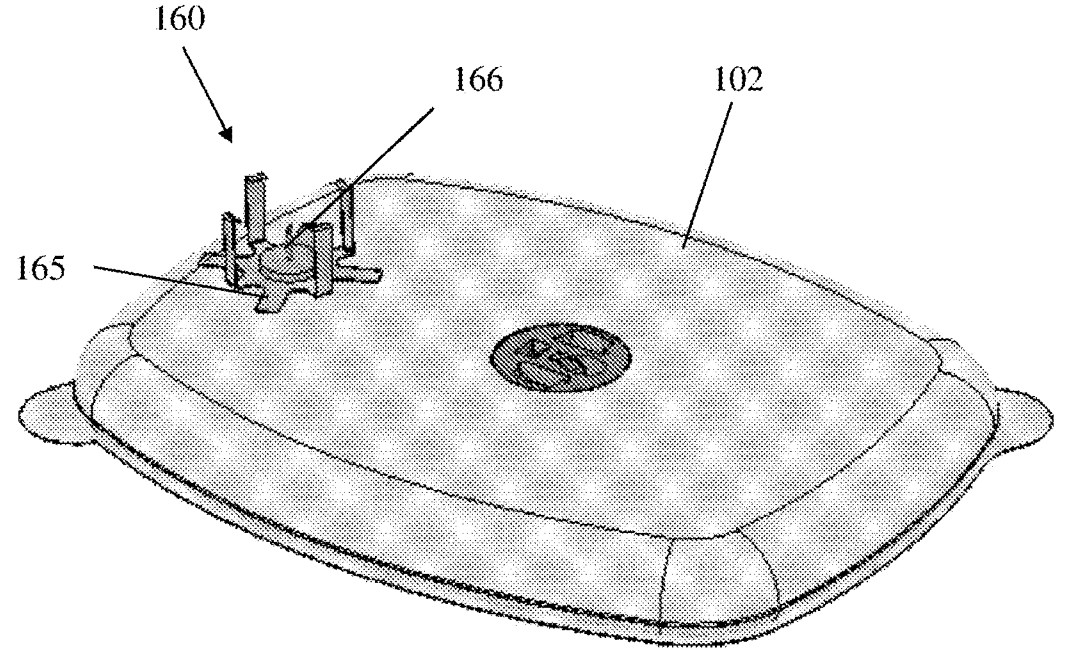
FIG. 13A is a schematic perspective view of a drug delivery device with a modular retaining clip and piercing needle shown disposed thereon according to one embodiment.
Figure 13B:
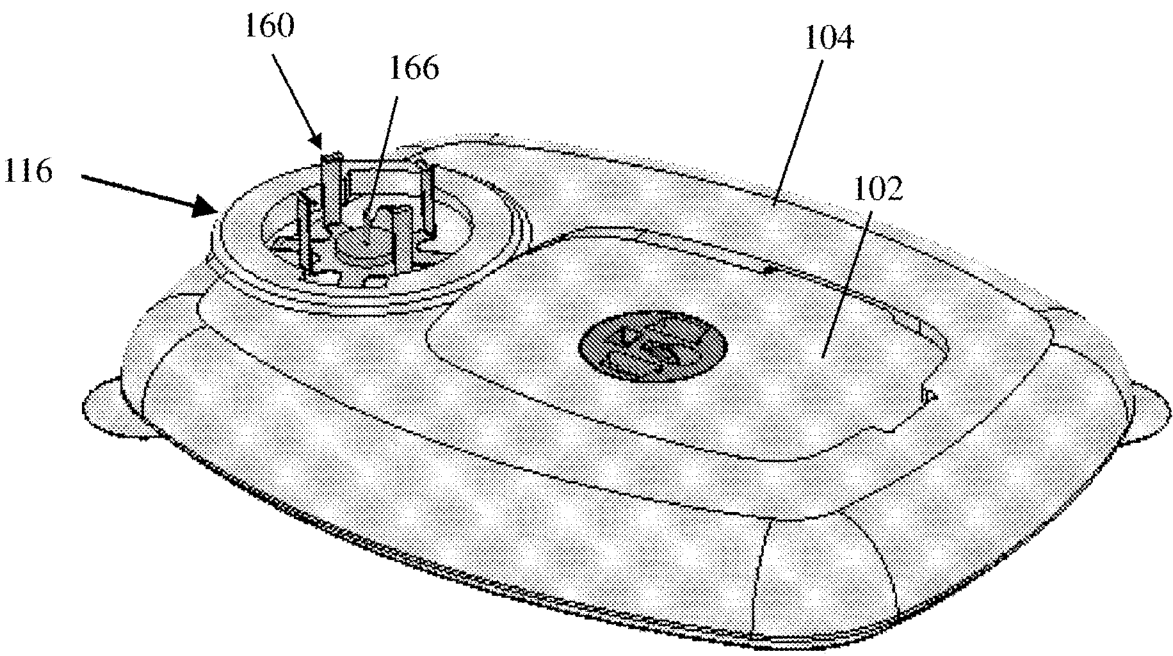
FIG. 13B is a schematic perspective view of the drug delivery device and retaining clip and piercing needle of FIG. 13A with a removable shroud housing shown disposed thereon according to one embodiment.

The retainer clip 160 may be attached to a drug delivery device as shown in FIG. 13A with a first end of the filling needle 160 been inserted into the septum 112 of the drug delivery device. The retainer clip may include stabilizers 165 that extend radially outwards from the hub and are positioned against an underlying surface of the drug delivery device. The stabilizers may stabilize and properly align the retainer clip to prepare the filling needle to connect with the filling device and pierce a septum of the container. The retainer clip 160 may also include latches 162 that extend outwards from the underlying surface of the drug delivery device and may be configured to engage with a portion of the filling device, including a neck of a container disposed in a filling device after the device has been actuated. Once the retainer clip is positioned on a drug delivery device, a separate housing 104 may then be coupled to the drug delivery device, as shown in FIG. 13B. The housing 104 may include an opening such as the opening depicted in the first alignment structure 116 that is sized and shaped for the retainer clip to extend through at least a portion of the opening.

Figure 14:
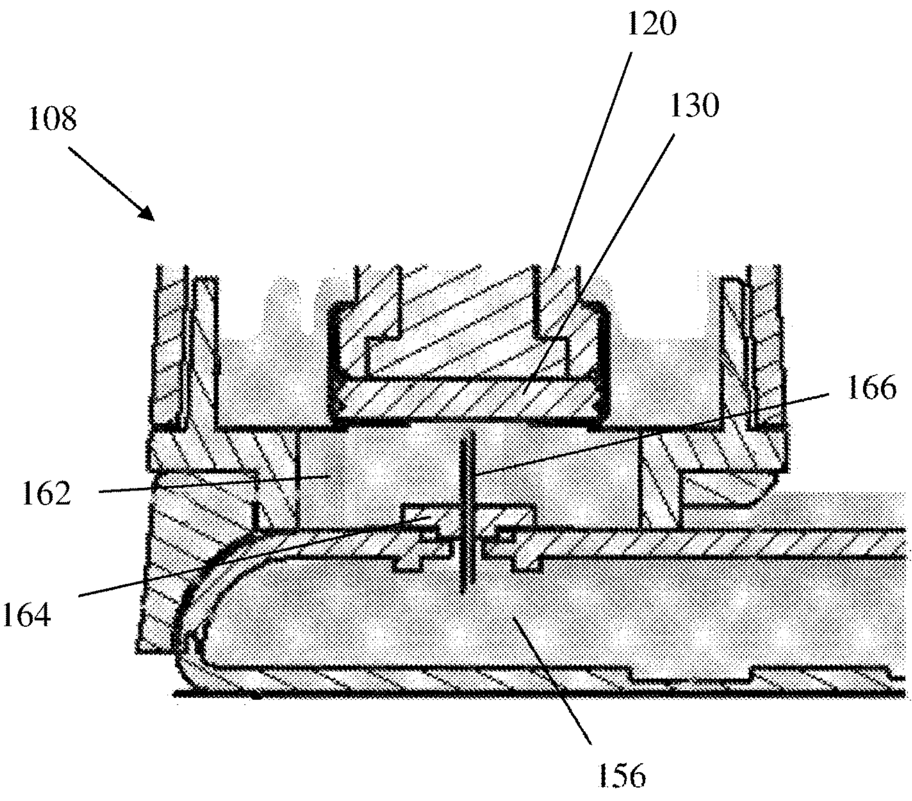
FIG. 14 is a schematic cross-sectional view of a drug delivery device with a retaining clip and associated piercing needle disposed on a drug delivery device with an associated filling device attached to the drug delivery device in an actuated configuration according to one embodiment.

FIG. 14 shows the filling device 108 connected to the drug delivery device and retainer clip 160. The filling needle 166 is inserted into the reservoir 156 and is aligned perpendicularly with the septum 130 of the container. The hub 164 retains a sterile connection and provides a planar surface for the septum 130 of the container to be displaced onto the needle. The latches 162 may also grip onto the neck of the container, or other portion of the filling device, after it has been deployed. Thus, the retainer clip 160 may be clipped onto the filling device 108 after use and may be removed with the housing 102 as a single assembly for disposal.

In the above embodiment, other than having the needle initially disposed on the drug delivery device, the drive system and overall operation are similar to that described above relative to FIGS. 4-10.

While the above embodiment illustrates how to dispense a therapeutic composition from a container including a piston, some containers are closed containers that do not include pistons. The following embodiments illustrate a way in which a therapeutic composition may be deployed from these types of containers as well.

Figure 15:
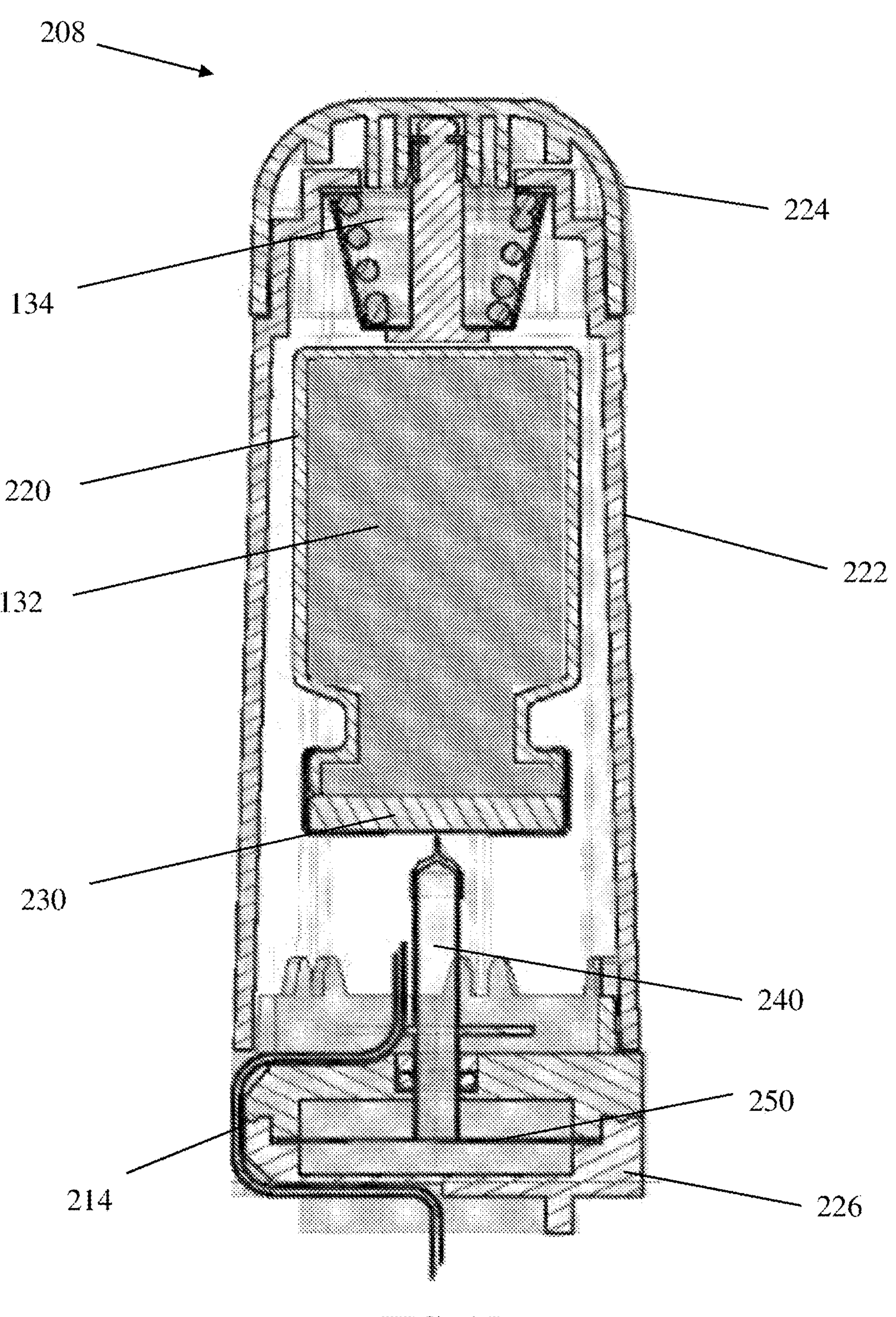
FIG. 15 is a schematic cross-sectional view of a filling device including an expandable membrane according to one embodiment.
Figure 16:
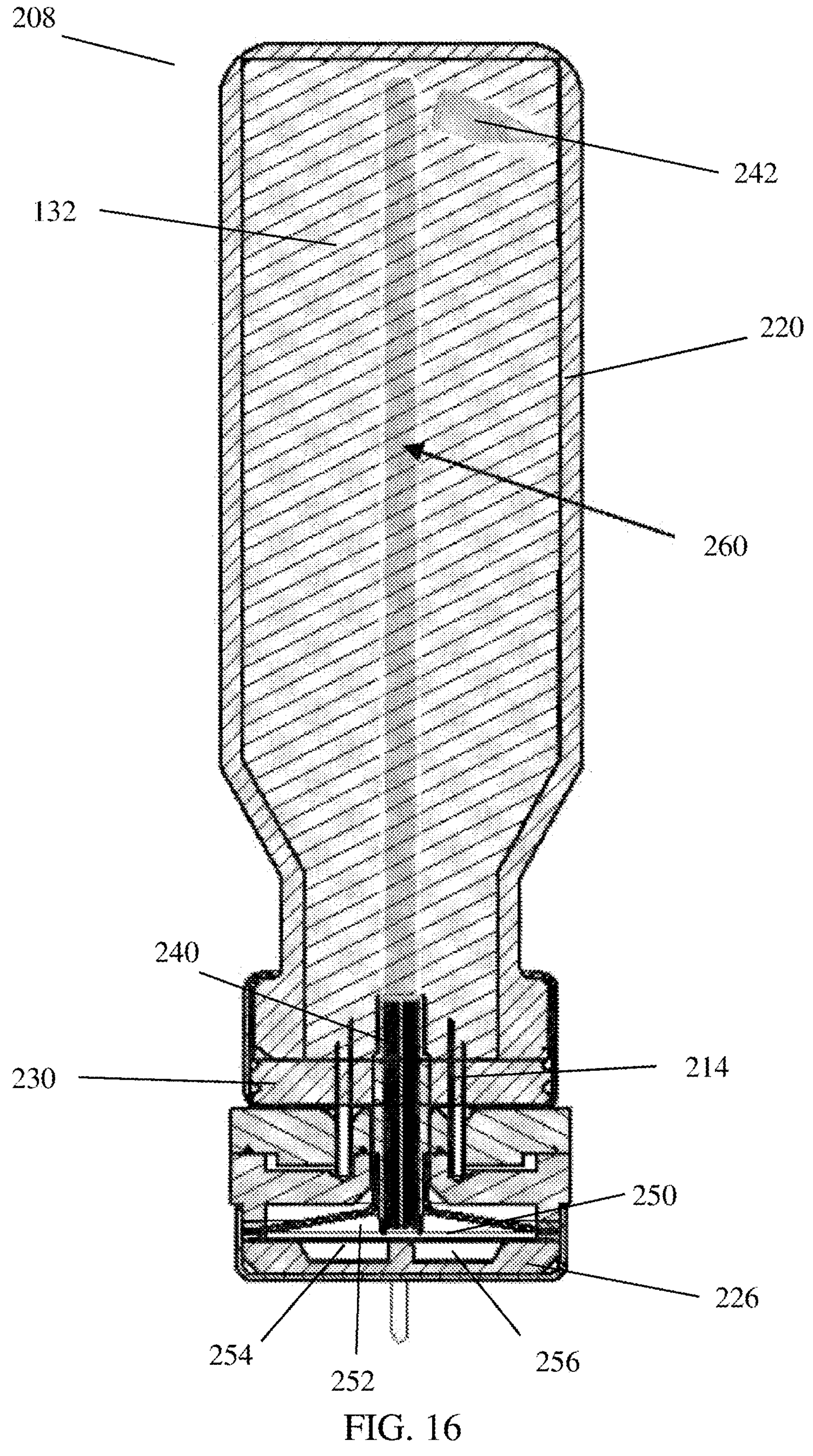
FIG. 16 is a schematic perspective cross-sectional view of a filling device after piercing of the septum of an associated container and during the initial expansion of an expandable membrane according to one embodiment.
Figure 17:
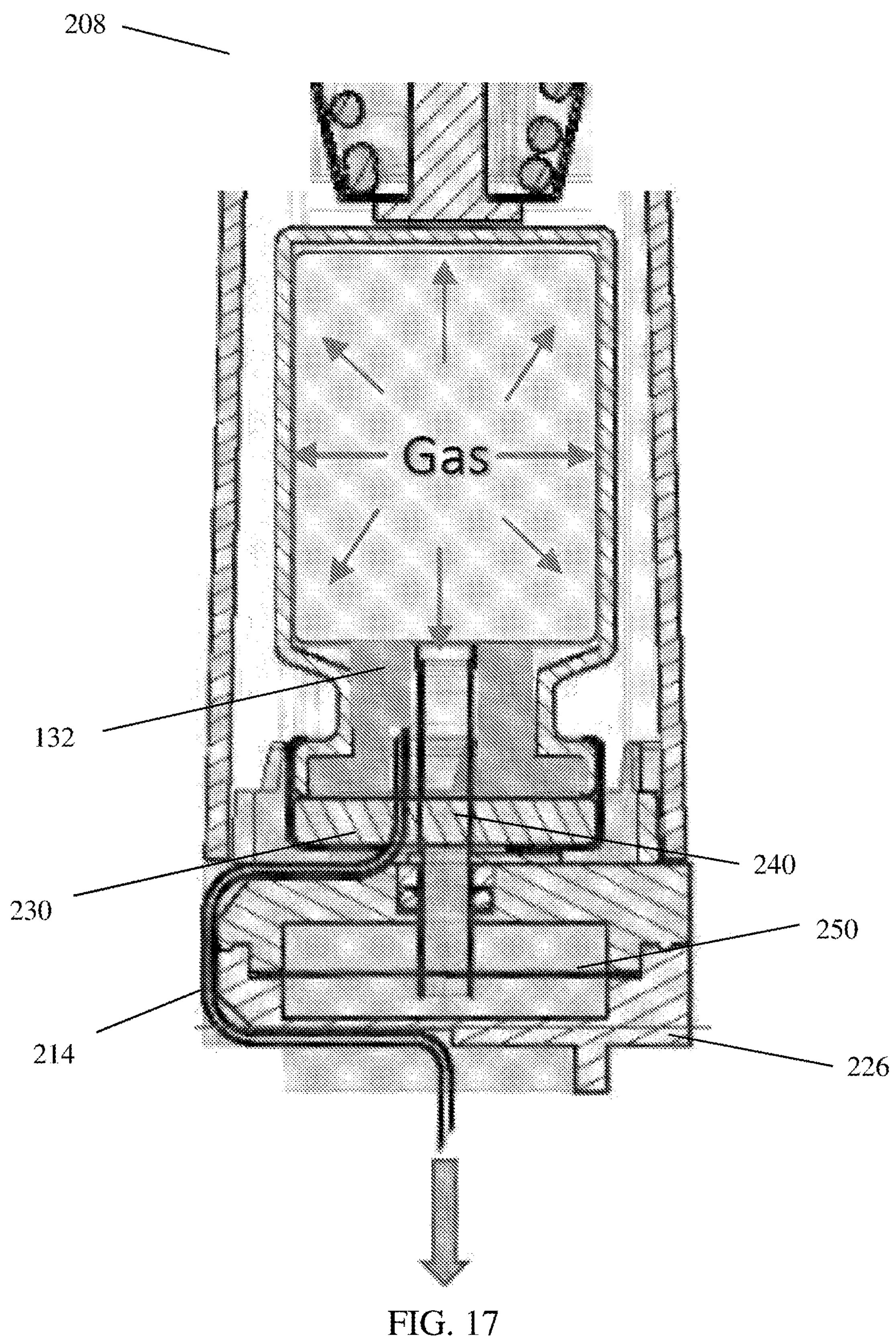
FIG. 17 is a schematic perspective cross-sectional view of a filling device after the expandable membrane has expanded within the interior of an associated container according to one embodiment.
Figure 18:
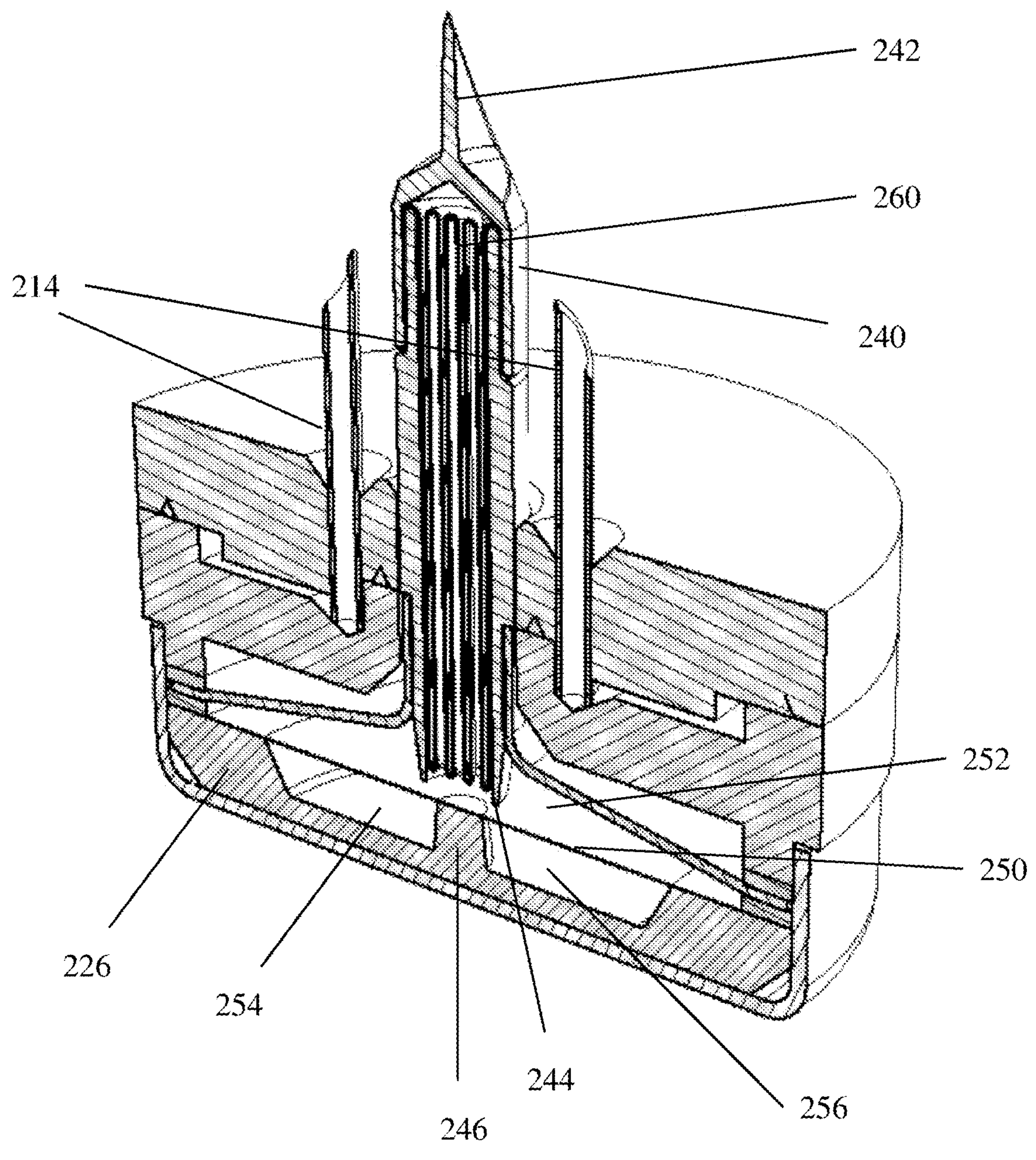
FIG. 18 is a schematic perspective cross-sectional view of the base portion of a filling device including a deployment mechanism for an expandable membrane according to one embodiment.

FIGS. 15-17 shows cross-sectional views of a filling device 208 according to an alternative embodiment. In some embodiments, the filling device 208 includes a main enclosure 222, a cap 224, and a base 226 similar to those described above with respect to the embodiment of FIG. 5. The filling device includes an interior volume sized and shaped to hold a container 220 containing a therapeutic composition 132 that is capable of being displaced within the filling device housing. The container may be an industry standardized closed vial container. The housing may also contain a drive system 143 similar to that described above with respect to FIGS. 5-8. When activated, the drive system may again displace the container 220 toward at least a filling needle 214 and a tube 240 that is positioned proximate to the filling needle and oriented towards the septum of the container. The needle may either extend to an exterior of the filling device, or may be in fluid communication with a separate needle that is in fluid communication with the device exterior through an intermediate volume. Also, as shown in FIG. 18, the base may include more than one filling needle, depending on the desired rate of flow of the therapeutic composition. In either case, both the one or more filling needles and the tube may pierce the septum 230 of the container when the drive system is actuated. However, due to the container not including a piston, the contents within the container remained unpressurized.

In view of the above, in some embodiments, the tube 240 includes an expandable membrane 260 that is disposed at least partially, and in some instances fully within, the tube in an initial unactuated configuration. After the septum 230 has been pierced by the tube, a pressurized gas may be used to expand the expandable membrane out of the tube 240 and into an interior volume of the container pressurizing the interior of the container. Due to the increased pressure of the container interior, the therapeutic composition is displaced out of the container 220 through the needle 214. In some embodiments, the needle 214 may be in fluid communication with a reservoir in a drug delivery device and the therapeutic composition 132 may flow out of the container into the reservoir. However, in other embodiments, the filling device may be an independent injection device, such as an autoinjector, and the therapeutic agent 132 may flow through the needle 214 directly into a patient.

In some embodiments, the tube 240 may include a separate piercing tip 242 that is removeable positioned on an end portion of the tube oriented towards the septum 230 of the container. The piercing tip may be sized and shaped to pierce the septum when the container is displaced onto the tube. The piercing tip may detach from the tube after it pierces the septum. Specifically, as noted above, in some embodiments, the tube may contain an expandable membrane 260 that, after the piercing tip pierces the septum, expands into an interior volume of the container to displace the therapeutic drug out of the container through the needle. This expansion of the membrane may force the piercing tip off of the tube into an interior of the container. The expandable membrane may be a thin-walled flexible membrane that is sealed to the inner surface of the tube and/or a chamber that the tube is in fluid communication with. Depending on the embodiment, the membrane may either be extensible or inextensible as the disclosure is not limited in this fashion.

FIG. 16 is a cross-sectional view of the device 208 after the expandable membrane 260 has expanded into the internal volume of the container 220. The piercing tip 242 of the tube has been pushed off the tube into the container interior. As the expandable membrane expands with increasing gas pressure, the therapeutic composition is displaced out of the container through the needle, as shown in FIG. 17. In accordance with some embodiments, the therapeutic composition is isolated from the gas which is contained within the impermeable expanding membrane. Thus, the therapeutic composition may only be in contact with the expanding membrane for the short duration of the fluid flow from the container reducing the risk of contamination.

While any appropriate method of providing a pressurized gas to expand the expandable membrane may be used, one embodiment of a method and construction to provide the desired gas is illustrated in FIG. 18. In the figure, a base 226 of the filling device 208 includes at least one needle 214 and a tube 240 as noted above. Additionally, in some embodiments, the base 226 may include a reaction chamber 252 that is in fluid communication with the tube. The reaction chamber may include a frangible barrier 250 separating the reaction chamber into a first volume 254 and at least a second volume 256, each containing chemical reactants. The frangible barrier may be a thin film laminate or other thin material that is easily fractured. The chemical reactants may include an acid and a base (e.g., potassium carbonate and citric acid), such that when they are mixed together, they generate a pressurized gas within the reaction chamber to expand the expandable membrane out of the tube and into the interior volume of the container. To facilitate breaking of the frangible barrier, in some embodiments, a base 226, or other portion, of the filling device that forms a portion of the reaction chamber beneath the frangible barrier may include a protrusion 246, or other structure, that mates with one or more piercing structures, such as the illustrated tapered edges of the tube disposed in the reaction chamber. For instance, the depicted protrusion fits within an interior of the tube. Such an arrangement may help to facilitate rupturing of the frangible membrane.

The volume of gas generated in a reaction chamber is determined by the type and relative amounts of the chemical reactants. This chemical reaction may initiate when the tube is displaced by a force being applied to the tube when the tube pierces a septum of the container. This displacement of the tube which may be mounted in a flexible component such as a flexible rubber septum fractures the frangible barrier allowing the reactants to mix and generate the desired gas in the reaction chamber. The expandable membrane expands or unfolds and rapidly moves into and expands within the inner volume of the liquid filled container as noted above. The continuous expansion and movement of the gas filled expandable membrane causes the liquid therapeutic composition to flow into the filling needle which may be fluidly connected to a reservoir 156 of a drug delivery device (see FIGS. 9-10).

Figure 19:
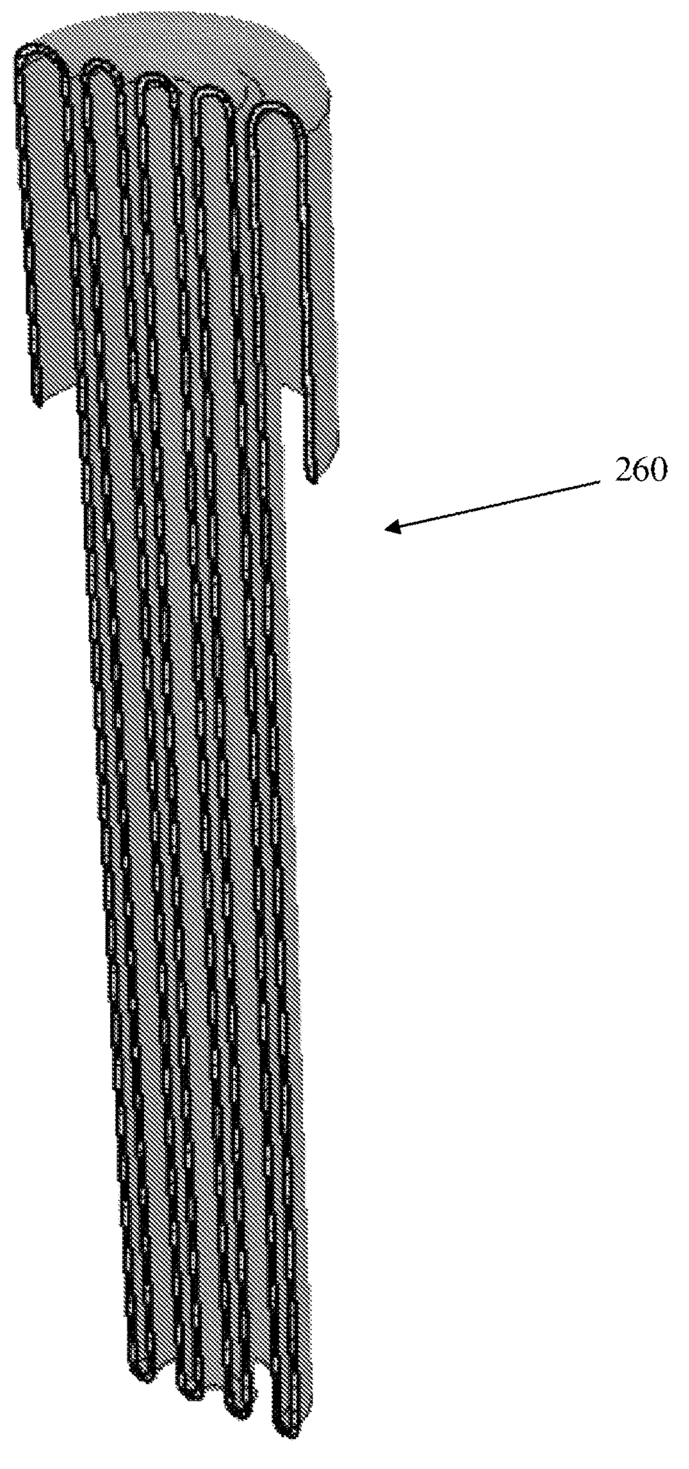
FIG. 19 is a schematic perspective cross-sectional view of an expandable membrane in an initial undeployed configuration according to one embodiment.
Figures 20A, 20B:
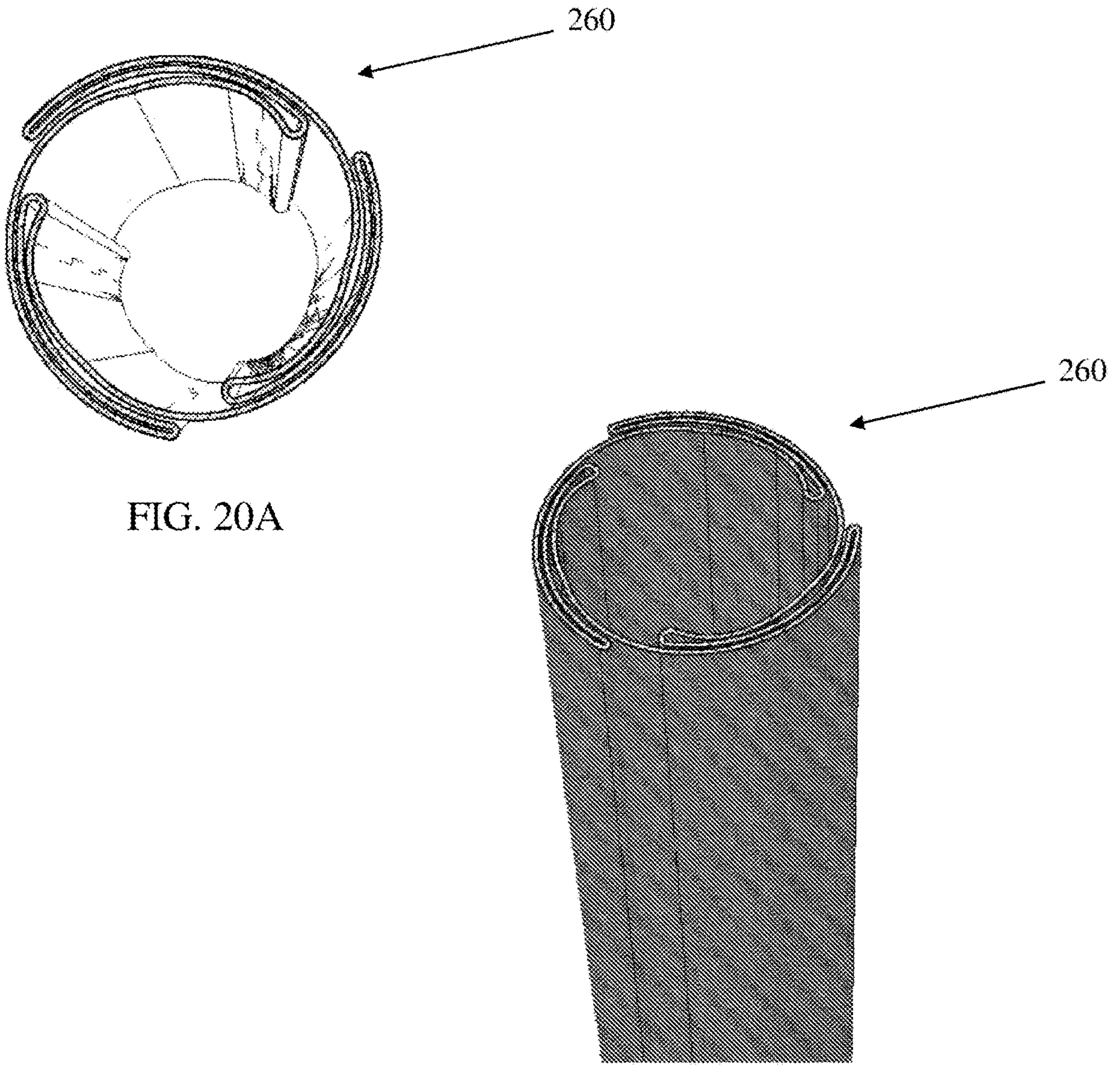
FIGS. 20A and 20B depict an expandable membrane in an initial undeployed configuration according to one embodiment.
Figures 21A, 21B:
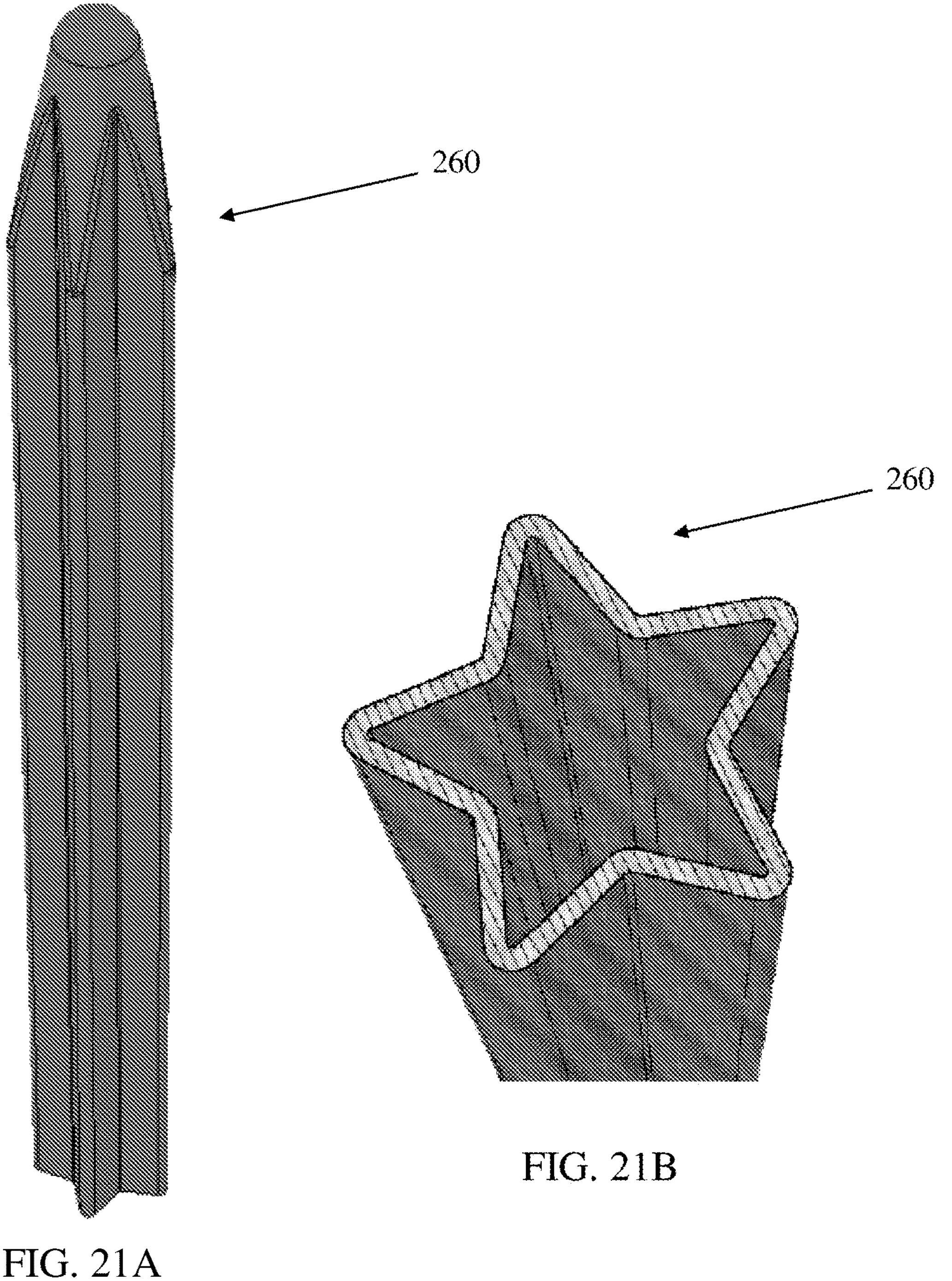
FIGS. 21A and 21B depict an expandable membrane in an initial undeployed, partially unfolded, configuration according to one embodiment.
Figure 22:
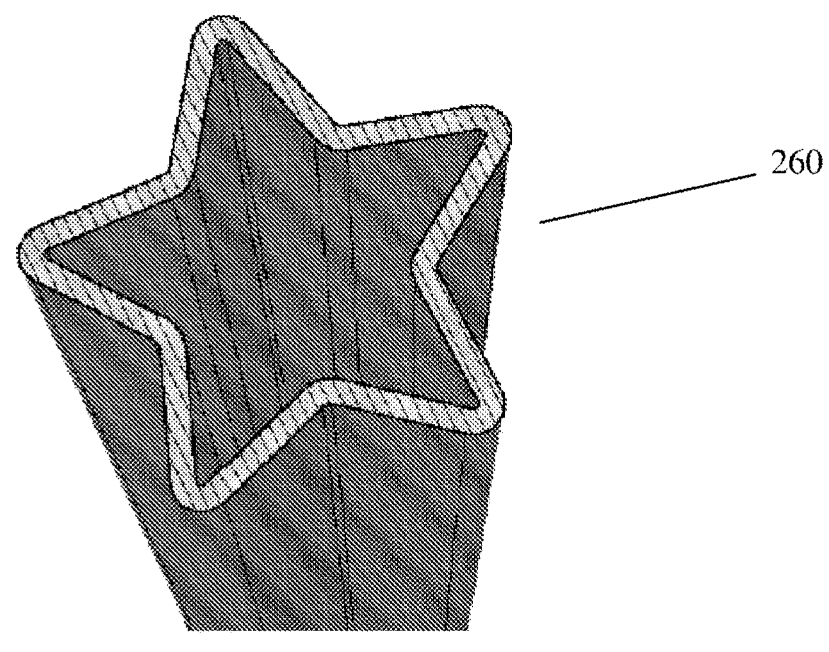
FIG. 22 depicts an expandable membrane in an initial partially folded undeployed configuration according to one embodiment.

In some embodiments, the expandable membrane 260 may be elastomeric, substantially inextensible, flexible, and/or any appropriate combination thereof. For example, flexible thin wall membranes such as flexible bladders and expandable balloon-like structure may be used. Additionally, many different shapes may be utilized, examples of which are shown in FIGS. 19-21. For example, geometric forms may include continuous membranes that are folded along their axial length in coaxially arranged folds may be used (FIG. 19). Overlapping folds relative to a cross sectional profile of a membrane may also be used (FIGS. 20A-20B). Additionally, membrane geometries that include radially inward oriented folds, such as expandable star cross sections, may be used too (FIGS. 21A-21B). Accordingly, it should be understood that any shape, folding geometry, and/or material may be used for an expandable membrane that allows for easy release from the tube and expansion into the container interior volume as the disclosure is not limited in this fashion.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

What is claimed is:

1. A device comprising:

a container configured to hold a therapeutic composition, the container comprising a first septum;

a needle;

a tube configured to be displaced to break a frangible barrier; and an expandable membrane disposed at least partially in the tube; and a reaction chamber including a first reactant and a second reactant separated by the frangible barrier, wherein the first reactant and the second reactant are configured to generate a gas when mixed after the frangible barrier is broken, wherein the container is configured to be displaced towards the needle and the tube to pierce the first septum of the container with the needle and the tube, and wherein when the tube pierces the first septum the expandable membrane is configured to expand out of the tube into an interior volume of the container to displace the therapeutic composition out of the container through the needle.

2. The device of claim 1, wherein the gas expands the expandable membrane out of the tube into an interior volume of the container to displace the therapeutic composition out of the container through the needle.

3. The device of claim 1, wherein the device is a filling device that is selectively couplable to a drug delivery device for filling a reservoir of the drug delivery device.

4. The device of claim 3, further comprising a lock including a first lock portion and a second lock portion, wherein the lock retains portions of a drive housing in a retracted configuration when in a locked configuration.

5. The device of claim 3, further comprising a removable housing coupled to the drug delivery device that can be removed with the filling device from the drug delivery device.

6. The device of claim 1, wherein the device is a filling device that further comprises a spring configured to displace the container towards the needle and tube.

7. The device of claim 1, wherein the tube comprises a piercing tip configured to be displaced off of the tube by the expandable membrane into an interior of the container when the tube pierces the first septum.

8. A method for expelling a therapeutic composition from a container, the method comprising:

piercing a first septum of the container with a needle and a tube, wherein piercing the first septum with the tube causes the tube to be displaced and break a frangible barrier separating a first reactant and a second reactant in a reaction chamber;

allowing the first and second reactants to mix and generate a gas in response to breaking the frangible barrier;

expanding a flexible membrane from the tube into an interior volume of the container using the gas to pressurize an interior volume of the container; and flowing the therapeutic composition out of the interior volume of the container through the needle.

9. The method of claim 8, wherein piercing the first septum comprises displacing the container toward the needle and the tube, and displacing the container applies a force to the tube that breaks the frangible barrier, and allowing the first and second reactants to mix and generate the gas to expand the flexible membrane out of the tube into the interior volume of the container to displace the therapeutic composition pressurizes the container to displace the therapeutic composition out of the container through the needle.

10. The method of claim 8, further comprising flowing the therapeutic composition through the needle into a reservoir of a drug delivery device.

11. The method of claim 8, wherein piercing the first septum of the container with the needle and the tube comprises displacing the container toward the needle and the tube.

12. A filling device selectively couplable to a drug delivery device, the filling device comprising:
- a container configured to hold a therapeutic composition, the container comprising a first septum;
- a needle;
- a tube; and
- an expandable membrane disposed at least partially in the tube,
- wherein the container is configured to be displaced towards the needle and the tube to pierce the first septum of the container with the needle and the tube, and wherein when the tube pierces the first septum the expandable membrane is configured to expand out of the tube into an interior volume of the container to displace the therapeutic composition out of the container through the needle; and
- a removable housing coupled to the drug delivery device, and configured to be removed with the filling device from the drug delivery device after providing the therapeutic composition to a reservoir of the drug delivery device.

13. A device comprising:
- a housing;
- a container disposed in the housing and configured to hold a therapeutic composition, the container comprising a first septum disposed on a first surface of the container; and
- a drive system operatively connected to container, wherein the drive system includes:
- a drive housing including a first drive housing portion and a second drive housing portion;
- a lock including a first lock portion associated with the first drive housing portion and a second lock portion associated with the second drive housing portion, wherein the lock selectively retains the first drive housing portion and the second drive housing portion in a first retracted configuration when the lock is in a locked configuration; and
- a mechanical potential energy source disposed in the drive housing between the first drive housing portion and the second drive housing portion, wherein when the lock is moved to an unlocked configuration, the mechanical potential energy source displaces the second drive housing portion to displace the container, and the first drive housing portion is a thrust plate and the second drive housing portion is a loading cup.

14. The device of claim 13, further comprising a needle oriented towards the first septum, and wherein when the mechanical potential energy source displaces the second drive housing portion and the container, the first septum is pierced by the needle.

15. The device of claim 13, further comprising a rotatable cap operatively coupled to the first or second portion of the lock, wherein when the cap is rotated, the lock moves to an unlocked configuration.

16. The device of claim 13, wherein the container includes a piston, and the second drive housing portion is disposed against the piston such that when the second drive housing portion is displaced, the second drive housing portion applies a force to the piston.

17. A device comprising:
- a housing;
- a container disposed in the housing and configured to hold a therapeutic composition, the container comprising a first septum disposed on a first surface of the container; and
- a drive system operatively connected to container, wherein the drive system includes:
- a drive housing including a first drive housing portion and a second drive housing portion;
- a lock including a first lock portion associated with the first drive housing portion and a second lock portion associated with the second drive housing portion, wherein the lock selectively retains the first drive housing portion and the second drive housing portion in a first retracted configuration when the lock is in a locked configuration; and
- a mechanical potential energy source disposed in the drive housing between the first drive housing portion and the second drive housing portion, and when the lock is moved to an unlocked configuration, the mechanical potential energy source displaces the second drive housing portion to displace the container, wherein the first lock portion is a slot formed in the first drive housing portion and the second lock portion is a mechanically interfering structure that is rotatably connected to the second drive housing portion, and the second lock portion is rotatable between the locked configuration and the unlocked configuration.

18. The device of claim 17, wherein the first drive housing portion is a thrust plate and the second drive housing portion is a loading cup.

19. The device of claim 17, wherein the second drive housing portion is configured to be displaced into a recess formed in a piston of the container.

20. The device of claim 13, further comprising a rotatable shaft extending between the second drive housing portion and the mechanically interfering structure.

* * * * *